United States Patent [19]

Dunn

[11] Patent Number: 5,681,581
[45] Date of Patent: Oct. 28, 1997

[54] CONTROLLED RELEASE PHARMACEUTICAL FORMULATIONS OF 3'-AZIDO-3'-DEOXYTHYMIDINE AND METHODS OF USE

[76] Inventor: James M. Dunn, 14 Inverness Dr. East, D-100 P.O. 3817, Englewood, Conn. 80112

[21] Appl. No.: 379,472
[22] PCT Filed: Aug. 4, 1993
[86] PCT No.: PCT/US93/07308
    § 371 Date: Mar. 27, 1995
    § 102(e) Date: Mar. 27, 1995
[87] PCT Pub. No.: WO94/03471
    PCT Pub. Date: Feb. 17, 1994

Related U.S. Application Data

[63] Continuation-in-part of Ser. No. 924,476, Aug. 4, 1992, abandoned.
[51] Int. Cl.⁶ .................. A61K 9/22; A61K 9/26; A61K 9/54
[52] U.S. Cl. .................. 424/468; 424/464; 424/469; 424/470; 424/490; 424/495; 424/497; 514/772.3
[58] Field of Search .................. 424/464, 465, 424/489, 493, 494, 468, 469, 470, 490, 495, 497

[56] References Cited

U.S. PATENT DOCUMENTS 4,917,900  4/1990  Jones et al. .................. 424/493

FOREIGN PATENT DOCUMENTS 10284407  9/1988  European Pat. Off. .

*Primary Examiner*—Thurman K. Page
*Assistant Examiner*—James M. Spear
*Attorney, Agent, or Firm*—Hale and Dorr

[57] ABSTRACT

This invention is directed to controlled release pharmaceutical formulations of 3'-azido-3'-deoxythymidine, also known as AZT or zidovudine and methods of use thereof. The controlled release formulations of AZT achieve and maintain a therapeutic level of AZT, while substantially reducing the side effects of AZT caused by its catabolite 3'-amino-3'-deoxythymidine (AMT) by reducing the amount of AMT produced.

16 Claims, 5 Drawing Sheets

CONTROLLED RELEASE PHARMACEUTICAL FORMULATIONS OF 3'-AZIDO-3'-DEOXYTHYMIDINE AND METHODS OF USE

CROSS REFERENCE TO RELATED APPLICATIONS

This application is a Section 371 application of PCT/US93/07308, filed Aug. 4, 1993, which is a continuation-in-part application of Ser. No. 07/924,476, filed Aug. 4, 1992, now abandoned.

BACKGROUND OF THE INVENTION

Field of the invention

This invention is directed to a controlled release pharmaceutical formulations of 3'-azido-3'-deoxythymidine, also known as AZT or zidovudine and methods of use thereof. The controlled release formulations of AZT achieve and maintain a therapeutic level of AZT, while substantially reducing the side affects of AZT caused by its catabolite, 3'-amino-3-deoxythymidine (AMT), by reducing the amount of AMT produced.

Retroviruses, AIDS and AZT

A virus is a biologic particle containing a nucleic acid core of DNA (deoxyribonucleic acid) or RNA (ribonucleic acid). The nucleic acid is surrounded by a protein membrane, the nucleocapsid. In some viruses there is another coat about the nucleocapsid, the envelope. The envelope is composed of vital specific proteins, lipids and carbohydrates. A viral particle is referred to as a virion.

When an infective virion enters the human body it adheres to a specific cell. This adherence is termed adsorption, which leads to a cell-virion attachment. After the virus particle attaches itself to a cell, it is transported into the cell where the envelope and the nucleocapsid are removed (uncoating). At this stage the virus is copied or replicated (replication). Transcription is the synthesis of RNA from DNA. To transcribe the viral nucleic acid into RNA, the enzyme transcriptase is required. In retroviruses, the nucleic acid is RNA. Therefore this process of transcription into DNA from RNA, is called reverse transcription and utilizes a specific enzyme, reverse transcriptase. This reverse enzyme transcription is the distinguishing feature of retroviruses.

Once in the form of DNA, the Genetic code of the virus is incorporated into the host DNA allowing it to take full advantage of the host cell's reproductive capabilities. The viral DNA incorporated into the host is virtually indistinguishable from the host DNA. Because of this, the viral code survives for the life of the cell.

A species of retroviruses was identified in the 1980's associated with the human disease, AIDS (Acquired Immune Deficiency Syndrome). The agent for this disease is called the HIV virus. (Human Immune Deficiency Virus). The HIV virus preferentially infects thymus derived lymphocytes (T4). HIV has a proclivity for these particular cells because they contain a protein coat, CD4, which preferentially binds with the HIV virus. Once infected, the immune cells decrease in number and lose their capability to produce an immune response.

There are a number of clinical manifestations of AIDS. In the initial stages when a person is infected, but does not have symptoms, they are sero-positive, referring to a positive blood test for the AIDS virus. It is in this sero-positive stage when people are carriers, capable of passing on the disease by blood transfusion, sexual intercourse or contaminated syringes. The patient may progress to the second stage, which is a persistent and chronic enlargement of their lymph nodes, or persistent generalized lymphadenopathy (PGL). In a further decline of their immune function, with a decrease in T4 cells, there is s a stage characterized by diarrhea, weight loss, fatigue and skin rashes. This condition is termed ARC (Aids Related Complex). The patient is termed as having Acquired Immune Deficiency Syndrome (AIDS). When the T4 cells fall below <200/ul, the symptoms can include fever persisting for more to than a month, involuntary weight loss of 10 percent of baseline, diarrhea lasting for more than a month or any series of opportunistic infections occur.

AIDS is a progressive, fatal disease. Currently the only Is approved primary treatment for AIDS is AZT (zidovudine). AZT is a synthesized chemical, 3'-azido-3'-deoxythymidine. Zidovudine was first identified in 1964 (J. P. Horowitz et al., *J. Org. Chem.*, 28:2076 (1964)). The compound was later found to have antiviral activity (E. DeClerq et al., *Biochem. Pharmacol.*, 29:1849 (1980). U.S. Pat. Nos. 4,724,232; 4,818,750; 4,828,838; 4,833,130; 4,837,208 and 4,874,609 describe uses, as well as synthesis methods, for zidovudine and its phosphorylated analogs and pharmaceutically acceptable salts. In the above cited patents, claims are made for the use of zidovudine as a treatment for human Acquired Immune Deficiency Syndrome (AIDS).

AZT is an inhibitor of reverse transcriptase, the intracellular enzyme responsible for the conversion of RNA to DNA as noted previously. The original dosage of the drug studied, based upon laboratory antiviral activity, was 200 mg every four hours. This dose, however, was too toxic and has subsequently been reduced to 100 mg given five times a day. AZT does not cure AIDS. As currently used, the drug has reduced the neurologic complications of AIDS and has decreased the morbidity associated with the disease.

AZT is commercially available as a powdered form of 3'-azido-3'-deoxythymidine. This product is converted by the body to a phosphate form. This phosphorylation process occurs within the cell where AZT is first converted to a monophosphate then to a diphosphate. The final step is a three phosphate or triphosphate form of AZT. It is this triphosphate form or "activated" form of zidovudine (AZT) which has the most inhibitory effect on vital transcription. This phosphorylation pathway is demonstrated in FIG. 1. Importantly, the amount of phosphorylated drug within the cells of HIV infected patients taking AZT showed no relationship between "activated," or phosphorylated AZT, and the dosage of drug given or the blood levels of AZT (Stretcher, B. N. et al., *Clin. Pharmacol. Ther.*, 49:198 (1992) and Stretcher, B. N. et al., *Clin. Pharmacol. Ther.*, 49:182 (1992)). The rate that the cells convert the AZT to its phosphorylated forms is therefore limited.

Importantly, new studies have demonstrated a breakdown product of AZT, AMT (3'-amino-3'-deoxythymidine) which is 5–7 times more toxic to bone marrow cells than AZT. The proposed enzymatic pathway for conversion of AZT to AMT is shown in FIG. 2. In addition, AMT, which has no antiviral activity, has an antagonistic effect on the anti-HIV action of AZT. The antagonistic effect is a result of competitive binding of the reverse transcriptase enzyme by AMT. The amount of AMT produced by intravenous regimens of AZT has been quantified (Stagg, P. M., et al., *Clin. Pharmacol. Ther.*, 51:668–676 (1993)). In clinical studies, patients were given intravenous AZT, 2.5 mg/kg, and the blood levels of all the metabolites, particularly AMT were measured. AMT was produced at about twenty percent of the level of AZT, as determined by the total area under the blood level time curve (AUC). Most importantly, this catabolite had a half life of 2.7 hours which was longer than that of the parent molecule. Because of this longer body dwell time, the product may be responsible for some of the toxic side effects seen with higher doses of AZT. The oral route of administration for AZT has produced higher levels of AMT in animals.

The first human studies on AZT treatment found that 1500 mg per day of AZT was not as effective as 500 mg per day of the drug in the treatment of asymptomatic patients who were sero-positive. Severe hematologic toxicity was also observed in this group of patients. (Volberding, P. A., New England J. Medicine, 322(14):941–949 1990). This result may represent toxicity of the AMT catabolite which would be produced in greater quantities with greater dosage of AZT. AMT was first synthesized in 1964 (Miller, N. and Fox, J. J., "Nucleosides XXI," J. Org. Chem., 19:1772–6 (1964)) and was found to have poor antiviral activity but potent anti-cancer effects. Other workers demonstrated that AMT 5'triphosphate is an inhibitor of HIV reverse transcriptase and also an inhibitor of DNA polymerase. All of these actions would result in AMT causing an increase in bone marrow toxicity while vitiating the antiviral activity of the phosphorylated AZT.

AZT Absorption and Distribution

Capsules and liquid solutions of orally administered AZT are rapidly absorbed from the gastrointestinal tract and converted by the liver to a glucuronide, GAZT (3'-azido-3'-deoxythymidine glucuronide), a water soluble conjugate that is excreted in the urine. As noted, AZT is also enzymatically reduced to AMT, (3'-amino-3'-deoxythymidine), a toxic catabolite. While the glucuronides of both AZT and AMT are excreted in the urine, the unconjugated AZT and AMT are distributed throughout the body and phosphorylated. Over a given period of time, greater amounts of AZT presented to the liver will produce proportionately greater quantities of AMT. Additionally, the more toxic AMT has a longer dwell time in the body than AZT. The present invention controls the input rate of AZT, thus decreasing the amount of AMP produced.

It is a continuing goal of researchers to be able to effectively treat HIV infected patients with AZT, while reducing the toxic side effects.

SUMMARY OF THE INVENTION

Figure 1:
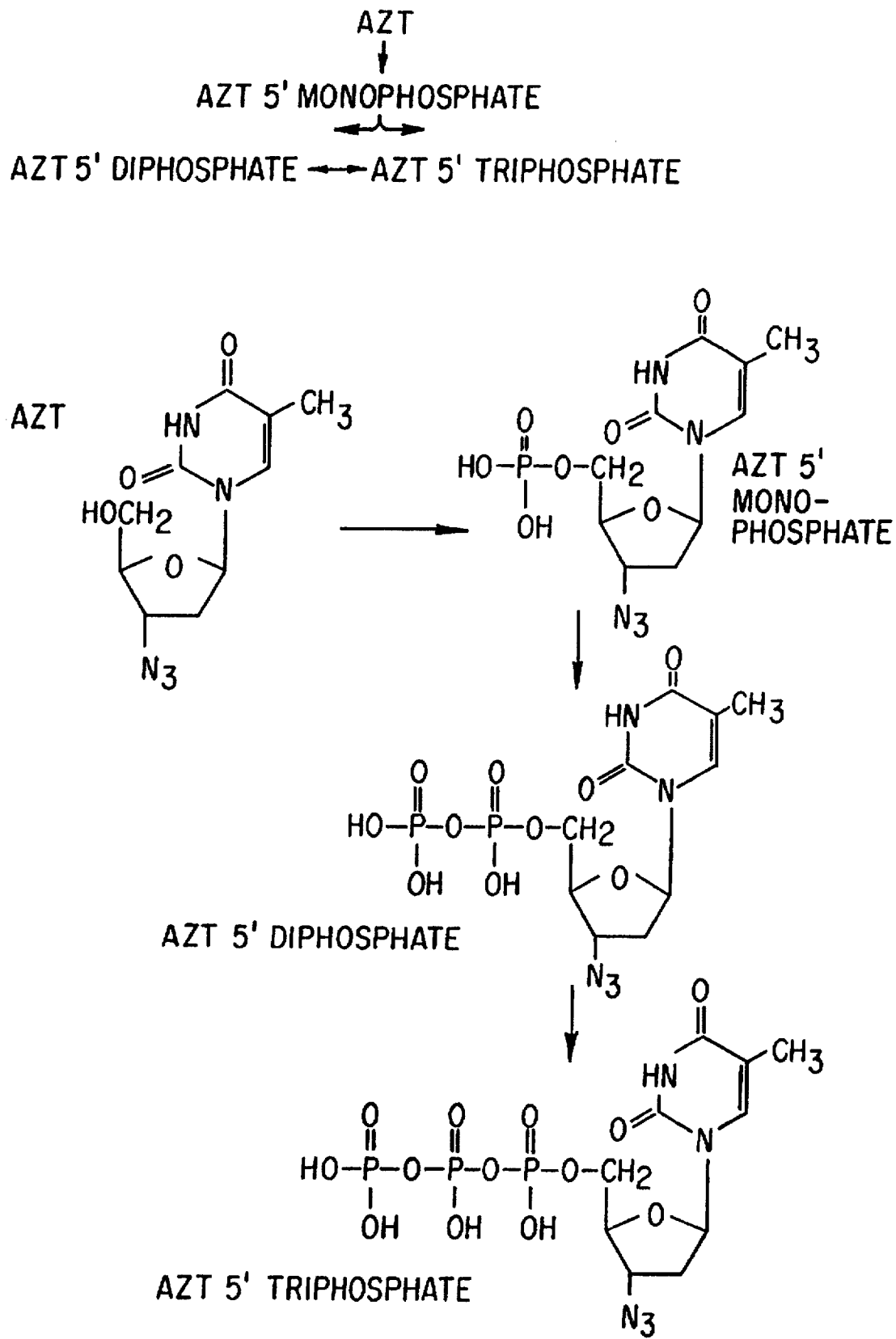
FIG. 1 demonstrates the chemical pathway for phosphorylation of AZT.
Figure 2:
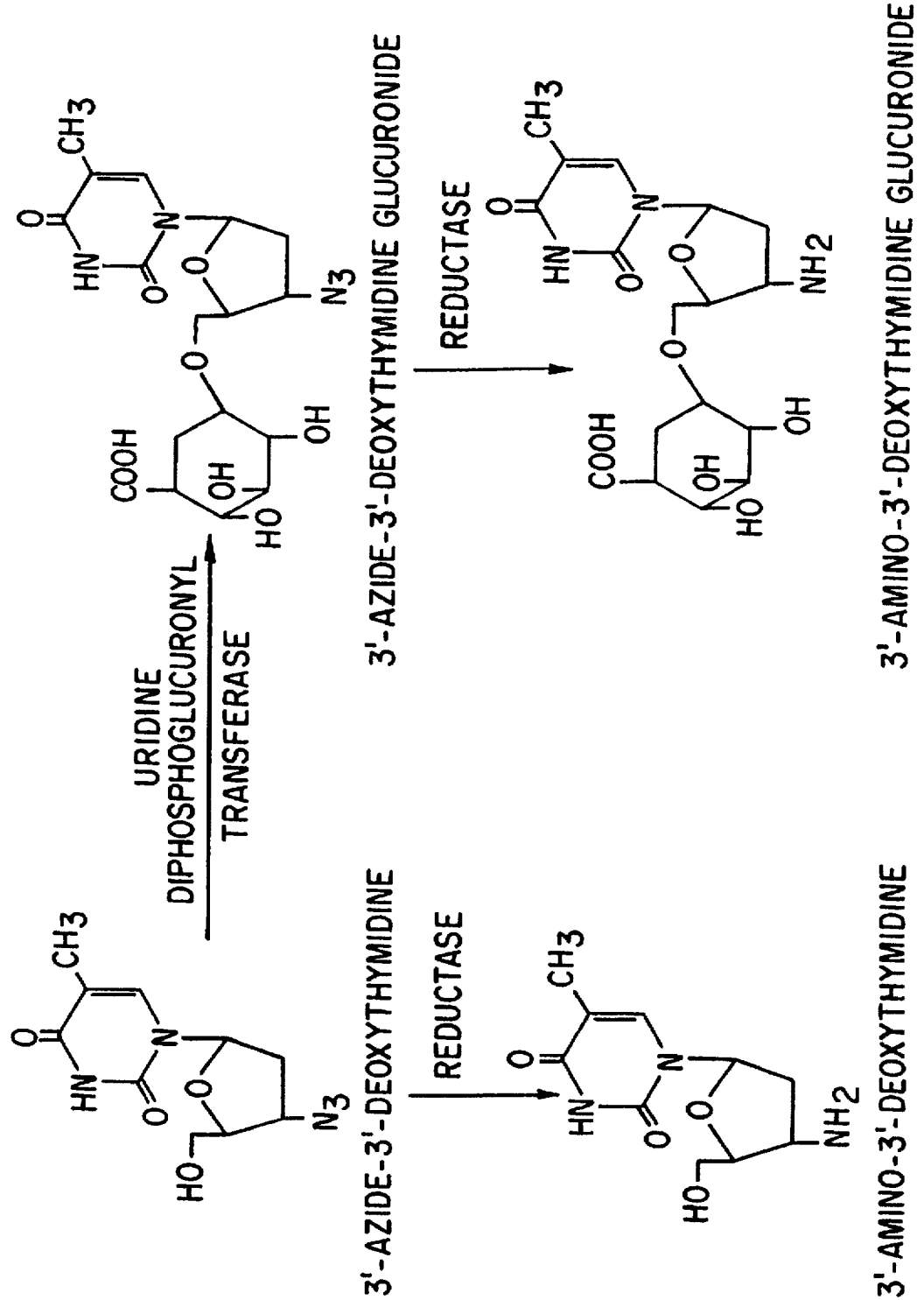
FIG. 2 outlines the enzymatic conversion path of AZT to AMT.

The inventor has discovered, through experimental analysis, that AZT can be formulated in a controlled release pharmaceutical preparation to achieve and maintain a therapeutic level of AZT, while substantially reducing the side affects of AZT caused by its catabolite 3'-amino-3-deoxythymidine (AMT) by reducing the amount of AMT produced.

The present invention is also directed to a method for treating HIV sero-positive patients, both symptomatic and asymptomatic, by administering to the patient the present controlled release formulation containing a therapeutically effective amount of AZT.

The present invention is further directed to a method for maintaining mean corpuscular volume (MCV) at <100 fl in HIV sero-positive patients by administering to the patient the present controlled release formulation containing a therapeutically effective amount of AZT released at a rate effective to maintain MCV at <100 fl.

The invention is also directed to methods for preparing the present controlled release formulation.

DETAILED DESCRIPTION OF THE INVENTION

Controlled release formulations are drug delivery systems in which the rate of the drug's release is maintained over an extended period of time. The controlled release formulations of this invention are orally administered controlled release dosage formulations containing a therapeutically effective amount of 3'-azido-3'-deoxythymidine (AZT) in which the AZT is released for intracellular phosphorylation at a rate that does not substantially saturate the uridine diphosphoglucuronyl-transferase pathway in converting AZT to glucuronide. When this pathway is substantially saturated, reductase will convert to the undesirable catabolite, 3'-amino-3-deoxythymidine (AMT) which has an antagonist effect on the reverse transcriptase inhibition of AZT. Preferably, AZT is released at a rate which results in mean serum levels of AMT at steady state of less than 25.0 ng/ml; more preferably less than 20 ng/ml; and most preferably less than 15.0 ng/ml. The uridine diphosphoglucuronyltransferase pathway is not substantially saturated when the patient exhibits no signs of clinical toxicity. Signs of clinical toxicity can be readily diagnosed by one of ordinary skill in the art and include for example, one or more of the following: vomiting; nausea; muscle pain; neuropathy; headache; diarrhea; and hematological toxicity including for example, an increase in mean corpuscular volume (MCV) to ≥100 fl, and anemia. The MCV in a normal adult is about 90±7 fl (Harrisons Text on Medicine, 12th ed., Appendix A10, (1991)). The present controlled release formulation releases AZT at a controlled rate effective to maintain MCV at <100 fl, and more preferably at about 90±7 fl. Further, the present controlled release formulation releases AZT at a controlled rate effective to maintain a viral particle concentration in a HIV sero-positive patient of less than 40,000 (forty thousand) virions per ml plasma, more preferably of less than 20,000 (twenty thousand) virions per ml plasma and most preferably a non-dectable amount. Viral particle concentration in a HIV infected patient is from about 10,000 (ten thousand) to about two million virions per ml plasma. IXth International Conference on AIDS/IVth STD World Congress, Jun. 7–11, 1993, *Comparison of Branched DNA Technology with Virus Culture for Quantitation of HIV-1 in Plasma*, R. Dewar, H. Highbarger, R. Davey, J. Metcalf, S-J. Fong and C. Pachl; and *Quantitation of HIV Plasma Viremia Using the Branched DNA Signal Amplification and p24 Antigen Assays During Combination Nucleoside Antiviral Therapy*, L. Bacheler, K. Ackerman, P. Sheridan, C. Pachl, K. Swanson and D. Winslow.

Additionally, the controlled release formulation of this invention releases AZT for intracellular phosphorylation at a controlled rate effective to maintain a therapeutic level of AZT. The phosphorylation of AZT to the monophosphate, diphosphate, and triphosphate forms proceeds in the cells at a rate that is independent from the blood serum levels of AZT. Thus, with this invention, the controlled release of AZT maintains the intracellular phosphorylation of AZT at a rate that will replace the amount of AZT being phosphorylated, metabolized and excreted from the body, while decreasing the amount of AMT produced.

The formulations are designed so that the administration of a single dosage unit provides the immediate release of an amount of AZT that promptly produces the desired therapeutic effect and the gradual release of additional amounts of the drug to maintain this level of effect over an extended period, usually from 8 to 12 hours.

The controlled release formulations of this invention reduce the drug blood level fluctuations. By controlling the rate of AZT release, the "peaks and valleys" of drug-blood or serum levels are substantially reduced. Further, the controlled release formulations reduce the dosing frequency. The rate-controlled AZT formulations deliver more than a single dose of medication and thus is taken less often than the current conventional form. These controlled release formulations also result in a substantial reduction in adverse side effects. Since the drug blood level does not substantially peak above the drug's therapeutic range, and into the toxic range, adverse side effects are less frequently encountered. There is also enhanced patient convenience and compliance. With less frequency of dose administration, the patient is less apt to neglect taking a dose. There is also the benefit of better patient convenience with daytime and nighttime medication, and control of chronic illness. Thus, in sum, the controlled release formulations of this invention achieve the goals of reduction in drug blood level fluctuations, reduction in dosing frequency, reduction in adverse side effects, as well as enhanced patient convenience and compliance.

Many sustained-release formulations are already known, but there is no generally applicable method by which such formulations can be designed. Generally speaking, each sustained-release formulation is dependent on the particular active substance incorporated therein. In designing a formulation, it is generally necessary to take into account many factors, including the rates of absorption and clearance of the active substance, the interaction of the active substance with the excipients and/or coating to be used in the formulation, the solubility of the active substance and of the excipients and/or coatings, and the effects on the bioavailability of the active substance which may be caused by the excipient and/or coatings. It is, however, not possible to readily predict whether any particular formulation will provide the desired sustained-release, and it is generally found necessary to carry out considerable experimentation to produce a sustained-release formulation having the desired properties.

The pharmaceutical formulation of the present invention is designed to release the active ingredients at a controlled rate over a specified period of time. The preferred formulation is a solid oral dosage form, preferably presented as a compressed tablet. The tablet, while primarily containing AZT, preferably in an amount of from 10 to 75 weight percent of the formulation and more preferably from 15 to 60 weight percent of the formulation, may be employed in combination with other therapeutic agents for the treatment of the HIV infection. Such other therapeutic agents are preferably present in an amount of from 0 to 50 weight percent of the formulation and more preferably from 15 to 35 weight percent. Examples of such further therapeutic agents include nucleoside analogs, such as, 2',3'-dideoxynucleosides such as 2',3'-dideoxycytidine, 2',3'-dideoxyadenosine and 2',3'-dideoxyinosine (DDI); acyclic nucleosides (e.g., acyclovir); interferons such as alpha-interferon; renal excretion inhibitors such as probenicid; nucleoside transport inhibitors such as dipyridamole; immunomodulators such as interleukin II; granulocyte macrophage colony stimulating factors; gancyclovir; phosphonates; and sodium or magnesium salts of phosphonates. The component compounds of such combination therapy may be administered simultaneously, in either separate or combined formulations, or at different times, e.g. sequentially such that a combined effect is achieved. The additional therapeutic agents may be granulated along with or separately from the AZT. Additionally, AZT and/or the other therapeutic agents may be dissolved in the polymer used to coat the granulate.

The active drug may be granulated along with known pharmaceutically acceptable excipients. Non limiting examples of excipients suitable for the formulation of the present invention include bulking agents including for example dibasic calcium phosphate (sold as Encompress® by the E. Mendel Co.); anhydrous lactose; and microcrystalline cellulose (sold as Avicel PH101® by the FMC Corp.). Preferably, the excipients are present in an amount of from 10 to 50 weight percent of the formulation, more preferably from 15 to 35 weight percent of the formulation. More specifically, dibasic calcium phosphate is present in an amount of from 0 to 20 weight percent of the formulation, and more preferably of from 5 to 15 weight percent. Anhydrous lactose is preferably present in an amount of from 0 to 25 weight percent and more preferably of from 8 to 20 weight percent of the formulation. Microcrystalline cellulose is preferably present in an amount of from 0 to 20 weight percent and more preferably of from 5 to 15 weight percent of the formulation.

The formulation provides a controlled release of the active antiviral compound (3'-azido-3'-deoxythymidine) or any pharmaceutically acceptable salt thereof, including phosphorylated forms. The drug particles are coated, along with excipients, with from 1 to 15 weight percent (weight percentages referred to throughout the specification, unless otherwise noted, are based upon the weight of the final, or theoretical weight of the finished granulate) of one or more acid resistant polymers, preferably from 3 to 13 weight percent. The preferred acid resistant polymers used for coating the drug granules include, but are not limited to cellulose acetate phthalate, hydroxypropylmethyl cellulose acetate phthalate, polyvinyl acetate phthalate, cellulose acetate trimellitate, and methacrylate copolymers in various forms sold as Eudragit® and more preferably include polyvinyl acetate phthalate, hydroxypropylmethyl cellulose phthalate and Eudragit®. Additionally, one or more hydrophobic and non-acid resistant agents may be used alone or in combination with one or more acid resistant polymers, for coating the granules, which agents include ethyl cellulose, zein, and certain methacrylate copolymers. The polymer coated granules may be coated with one or two additional acid resistant and/or hydrophobic polymer coats depending on the rate of release of active drug desired. AZT and/or the additional therapeutic agents set forth above can also be incorporated in these additional polymer coats.

The polymer coated granules are then incorporated into a lipid hydrogel polymer matrix. The lipid comprises from 1 to 10 weight percent of the formulation and preferably from 3 to 8 weight percent. Suitable lipids include for example, fixed oils and fats; waxes; sterols; phospholipids; and glycosides. The preferred lipid being hydrogenated cottonseed oil (Lubritab® by E. Mendel Corporation).

Suitable fixed oils and fats include polyunsaturated and saturated glycerides, i.e., glycerol stearate, coco-butter; oils including castor oil, cod liver oil, corn oil, cottonseed oil, peanut oil, sesame seed oil, olive oil, mineral oil, and white oil, and their hydrogenated derivatives; glycerol trioleate, glycerol tripalmitate, and glycerol monosterate; and fatty waxes and their hydrogenated components.

Suitable waxes include for example, carnauba wax, cetyl esters, lanolin, white wax, yellow wax, and sterols having fatty acid esters in the place of a trihydric alcohol.

Suitable sterols include for example, cholesterol and its derivatives. Sterols are alcohol components of steroids. In the classification of sterols, R' is an aliphatic side chain in the cyclopenatherene ring. A classical function of natural sterols is a 3-hydroxyl in a beta orientation.

Suitable phospholipids include any known phospholipid, i.e., lecitihins. Phospholipids are lipoidal constituents that contain phosphorus in their molecules. Lecitihins are phospholipids that yield two molecules of fatty acid and one molecule of glycerol, phosphoric acid and a basic nitrogen compound.

Suitable glycosides include any known glycoside.

One or more hydrogel polymers are present in a total amount of from 1 to 20 weight percent and preferably from 3 to 15 weight percent of the formulation. Hydrogel polymers are suspensions made up of small particles which are dispersed by an essentially aqueous media. Suitable hydrogel polymers include for example, carbomer, alginic acids and the salt derivatives thereof, gelatin, guar gum, hydroxyethyl cellulose, hydroxypropyl methylcellulose, methycellulose pectin, carboxymethylcellulose, powered cellulose and gum acacia. One preferred hydrogel polymer is carboxypolymethylene, an acrylic acid polymer (carbomer) sold under the mark Carbopol-934-P® by B.F. Goodrich. Additionally, a second polymer which may be used is a high viscosity hydroxypropylmethyl cellulose derivative sold as Methocel 4KM-P® by Dow Chemical Corporation.

In one embodiment of the present invention, the granules having one or more polymer coats provided thereon and containing the active drug are incorporated into a matrix containing the lipid and the hydrogel polymers. In another embodiment, the lipid and the hydrogel polymers are comprised in the granules having one or more polymer coats provided thereon.

The formulation may additionally contain one or more bulking agents, disintegrants and lubricants. Bulking agents are agents which are used to increase the total tablet size and are preferably present in an amount of from 0 to 50 weight percent of the formulation and include for example, mannitol, sorbitol, calcium phosphate and sulfate in the dibasic and tribasic forms both hydrous and anhydrous, lactose, calcium carbonate, sodium starch glycolate, sodium stearate, and propylene glycol. Suitable disintegrants are preferably present in an amount of from 0 to 20 weight percent of the formulation and are preferably from 0.5 to 10.0 weight percent, and include for example, sodium starch glycolate and starch 826. Suitable lubricants include Lubritab®, and magnesium stearate, and are preferably present in an amount of from 0 to 5 weight percent of the formulation. The present formulation may also include one or more anti-adherant agents provided in the polymer coating solution used to coat the granules or the solution used to film coat the final tablet. Such anti-adherants agents include steric acid and other long chain fatty acids preferably in an amount of from 0.25 to 1.5 weight percent of the formulation when coating granules, and from 0.25 to 5.0 weight percent of the film coating formulation.

In the preferred embodiment, the formulation is a compressed tablet which may be film coated with acid resistant or hydrophobic film coating agents. Such polymers may include coloring pigments as well as plasticizers. Preferred coating polymers include ethyl cellulose, polyvinyl acetate phthalate, hydroxypropylmethyl cellulose phthalate, cellulose acetate phthalate, cellulose acetate trimellitate, methacrylate such as the various copolymers produced and marketed as Eudragit®. The preferred acid retardant coating is polyvinyl acetate phthalate, PVAP. The amount used for the coating is from 1 to 7 weight percent of the final granulate with the preferred amount being from 2 to 4 weight percent, with a suitable plasticizer.

Suitable plasticizers for use in the present invention include for example, any accepted agents such as acetyldiethyl citrate, glycerin, triacetin, diethyl phthalate, dimethyl phthalate, and polyethylene glycol. The amount of plasticizer per weight of polymer may range from 0.25 to 5.00 weight percent but is more preferably 0.5 to 2.0 weight percent.

The formulation of this invention retards the release of the active drug or drugs in the gastric juice via the acid retardant polymer coating. These polymers slowly dissolve in the alkaline media of the small intestine. At this time the lipid hydrogel matrix becomes hydrated and swells producing a diffusion membrane which further slows the solvation rate of the active drugs and their subsequent absorption. This lipid hydrogel matrix serves as a secondary membrane to control the diffusion of the active agent from the tablets.

Additionally, the active agents, their pharmaceutical salts or phosphorylated forms can be granulated into two or more fractions. The first fraction contains active material coated with a polymer which releases more quickly than the polymer coating of the granules of a second or a third fraction. Suitable polymers include polyvinyl acetate phthalate, hydroxypropylmethyl cellulose phthalate, cellulose trimellitate acetate, and methacrylate copolymers. The first fraction contains a plasticizer appropriate for the polymer being used preferably in an amount of from 0.25 to 5.0 weight percent of the polymer, more preferably from 0.5 to 2.0 weight percent of the polymer, and the polymer is present in an amount of from 1 to 15 weight percent and more preferably from 3 to 13 weight percent. The second fraction contains active material coated with a polymer that releases in a more alkaline media. Suitable polymers for use in this second fraction include hydroxypropylmeyhyl cellulose phthalate, low permeability methacrylate copolymers, ethylcellulose and zein. Preferably, these polymer coats are present in an amount of from 1 to 10 weight percent and more preferably from 3 to 8 weight percent. The fractions coated may be equal in amount or the ratio may be varied depending upon the delivery pattern to be achieved.

Turning to the preferred process of the present invention, all materials are weighed and screened through a number

20 mesh sieve to ensure uniformity of particle size. The preferred method of granulation is with a fluidized bed dryer. The active agents and excipients are blended in the fluid bed dryer for fifteen minutes at a temperature of 40° C. The polymer coating solution is then sprayed into the fluid bed with continuous fluidization at 40° C. and at an atomizing pressure of 0.5–1 bars and a rate of 2 grams per minute. The spraying rate may be changed depending upon the degree of hydration observed in the material being granulated. In most instances, aqueous solvent systems are preferable. When an organic solvent is used, the polymer volatilization rate may be faster and subsequently the infusion rate of the polymer may be increased. Suitable organic solvents include DMSO.

The present formulations can be prepared in any controlled release form. Preferably, the present formulations are prepared in a controlled release form suitable for oral administration including for example, discrete units such as capsules, cachets, or tablets each containing a predetermined amount of the active ingredient AZT, or as a powder or granules. The present formulations may also optionally include a pharmaceutically acceptable carrier, binder, lubricant, inert diluent, preservative, disintegrant, surface-active or dispersing agent, sweeteners, thickeners, and flavoring agents. Tablets may optionally be provided with an enteric coating. Preferably, the present controlled release formulation is in a solid dosage form containing granules of the active drug containing AZT.

One of ordinary skill in the art to which the present invention pertains can readily determine appropriate dosage amounts as well as frequency of administration and duration of the course of treatment. In General, a therapeutically effective dose will be in the range of from 1.0 to 20.0 mg per kilogram body weight per day, preferably in the range of 1.0 to 15.0 mg per kilogram body weight per day, and most preferably in the range of 3.0 to 7.0 mg per kilogram body weight per day. The desired dose is preferably presented as one or more sub-doses, more preferably one, two or three sub-doses, and most preferably two sub-doses, administered at appropriate intervals throughout the day. These sub-doses may be administered in unit dosage forms, for example, containing a therapeutically effective amount, more specifically containing 100 to 1000 mg, preferably 200 to 800 mg, and most preferably 250 to 500 mg of the active ingredient AZT per unit dosage form.

Preferably, the active ingredient, AZT, should be administered to achieve peak plasma concentrations (at the second to fifth hour after drug administration) of the active compound AZT, of less than 700 ng/ml, preferably from about 200 to 400 ng/ml, and most preferably from about 100 to about 350 ng/ml.

The present invention is also directed to a method for preparing a controlled release rate solid oral dosage formulation containing an active drug which drug contains a therapeutically effective amount of AZT, zidovudine (3'-azido-3'-deoxythymidine), its phosphorilated forms or pharmaceutically acceptable salts thereof. The method is carried out by: (a) blending the active drug with one or more pharmaceutically acceptable excipients to form a mixture; (b) dividing the resultant mixture of step (a) into one or more fractions; (c) separately granulating each of the one or more fractions of step (b) to form one or more granulated fractions; (d) coating the granules of each of the one or more granulated fractions of step (c) with one or more polymeric coats applied serially, each of the polymeric coats containing one or more members selected from the group consisting of an acid resistant polymer and a hydrophobic polymer, to form coated granules; and (e) blending the resultant coated granules of step (d) with one or more hydrogel polymers and with one or more lipids, to form a final mixture.

Moreover, the present invention provides a method for preparing a controlled release rate solid oral dosage formulation containing an active drug which drug contains a therapeutically effective amount of AZT, zidovudine (3'-azido-3'-deoxythymidine), its phosphorylated forms or pharmaceutically acceptable salts thereof. The method is carried out by: (a) blending the active drug with one or more hydrogel polymers, one or more lipids and one or more pharmaceutically acceptable excipients to form a mixture; (b) granulating the resultant mixture of step (a) to form granules; and (c) coating the resultant granules of step (b) with one or more polymeric coats applied serially, each of said polymeric coats comprising one or more members selected from the group consisting of an acid-resistant polymer and a hydrophobic polymer, to form a final mixture.

In both the foregoing and the above methods the final mixture is further processed into a dosage form, i.e., a solid dosage form such as a tablet.

The following examples further describe the materials and methods used in carrying out the invention. The examples are not intended to limit the invention in any manner.

EXAMPLE 1

Tablets weighing 500 mg and containing 300 mg of AZT were prepared in the following manner.

| Ingredients | Percent (%) | mg/tab | 1.5 ng |
|---|---|---|---|
| 1. AZT | 60.0 | 300.0 | 0.900 |
| 2. Encompress ® | 14.0 | 70.0 | 0.210 |
| 3. Avicel PH101 ® | 6.0 | 30.0 | 0.090 |
| 4. Cellulose Acetate Phthalate | 4.0 | 20.0 | 0.060 |
| 5. Triacetin | 1.0 | 5.0 | 0.015 |
| 6. Stearic acid | 1.0 | 5.0 | 0.015 |
| 7. Carbopol 934-P ® | 4.0 | 20.0 | 0.060 |
| 8. Methocel 4KM-P ® | 4.0 | 20.0 | 0.060 |
| 9. Lubritab ® | 4.0 | 20.0 | 0.060 |
| 10. Magnseium Stearate | 0.5 | 2.5 | 0.008 |
| 11. Starch 826 | 1.5 | 7.5 | 0.022 |
|  | 100.0 | 500.0 | 1.500 |

Ingredients 1–3 (Encompress® is dicalcium phosphate (a binding agent) sold by E. Mendel Co.; Avicel PH101® is microcrystalline cellulose sold by the FMC Corp.), after screening and blending, were divided into equal weights A and B. The "A" fraction was granulated in the fluid bed dryer at 40° C. using 50 grams of cellulose acetate phthalate in 200 ml of ammoniated deionized water with 4 grams of triacetin and steric acid. Following this, fraction "B" was granulated with cellulose acetate phthalate (CAP), 50 grams in 200 ml of ammoniated deionized water with steric acid and 4 grams of triacetin as a plasticizer. After both granulations were dried to less than <1% moisture content, they were blended with Carbopol-934-P®, Lubritab®, Methocel 4KM-P® Dow Chemical, magnesium stearate, and starch 826. After 2–3 minutes of blending, the materials were passed through an #18 mesh screen and further blended in the fluid bed dryer for 3 minutes. The blended and lubricated granulate was then compressed into tablets, using a 16 station rotary tablet press. The tablet fracture force strength is 15–20 kg and the tablet weight was 500 mg±25 mg.

EXAMPLE 2

Tablets weighing 800 mg and containing 250 mg of AZT and 250 mg of acyclovir are prepared in the following manner.

| Ingredients | Amount (grams) |
| --- | --- |
| 1. Zidovudine (AZT) | 312 |
| 2. Acyclovir | 312 |
| 3. Dibasic Calcium Phosphate | 100 |
| 4. Anhydrous Lactose | 96 |
| 5. Eudragit RS 30D* | 60 |
| 5. Acetyldiethyl citrate | 8 |
| 6. Carbopol 934-P ® | 40 |
| 7. Methocel 4KM-P ® | 40 |
| 8. Hydrogenated Cotton Seed Oil | 30 |
| 9. Magnesium Stearate | 2 |

*Eudragit RS 30D ® is a latex dispersion of copolymers of acrylic and methacrylic acid esters.

AZT, acyclovir, lactose and dibasic calcium phosphate are screened through a number #20 mesh screen and blended in a fluid bed dryer at a temperature of 40° C. for 15 minutes. The Eudragit RS 30D® with acetyldiethyl citrate is sprayed into the fluid bed using a Watson Marlow peristaltic pump at a rate of 2 grams per minute and an atomizing pressure of 0.5–1 bar. After granulation is complete, the granulate is dried until the s moisture content is less than 1%. The Methocel and Carbopol 934-P® are screened along with the magnesium stearate through a #20 mesh screen and blended with the granulated active agent. The granulate is then compressed to a weight of 800 mg±25 mg with a hardness of 15–25 kg.

EXAMPLE 3

Film coated tablets weighing 600 mg and containing 300 mg of AZT were prepared in the following manner.

| Ingredients | Amount (grams) |
| --- | --- |
| 1. Zidovudine (AZT) | 500 |
| 2. Dibasic Calcium Phosphate | 130 |
| 3. Anhydrous Lactose | 110 |
| 4. Cellulose Acetate Phthalate | 60 |
| 5. Triacetin | 8 |
| 6. Carbopol 934-P ® | 60 |
| 7. Methocel 4KM-P ® | 60 |
| 8. Hydrogenated Cotton Seed Oil | 70 |
| 9. Magnesium Stearate | 2 |

AZT, lactose and dibasic calcium phosphate were screened through a number #20 mesh screen and blended in a fluid bed dryer at a temperature of 40° C. for 15 minutes. The cellulose acetate phthalate was dissolved in ammoniated deionized water with triacetin. The AZT along with lactose and dibasic calcium phosphate were granulated by spraying the polymer (CAP) under a pressure of 0.5–1 bar at a rate of 3 grams per minute while the material was fluidized at a temperature of 40° C. After the granulation was completed the granulate was further dried until the moisture content was less than 1%. The Methocel and Carbopol 934-P® were screened along with the magnesium stearate through a #20 mesh screen and blended with the granulated active agent. The granulate was then compressed on a tablet press to a weight of 600 mg±25 mg with a hardness of 10–15 kg.

The core tablets, 1000 grams, were then charged into a Vector HCT-30 film coater. The tablets were heated to 32° C. and tumbled at 25 rpm's. A coating solution was prepared in the following manner.

| Ingredients | Amount (grams) |
| --- | --- |
| 1. Polyvinyl Acetate Phthalate | 30 |
| 2. Ammoniated deionize water | 200 |
| 3. Triacetin | 3 |
| 4. Titanium dioxide | 2 |
| 5. Stearic Acid | 5 |

The polyvinyl acetate phthalate was dispersed in ammoniated deionized water with a high speed Silverson mixer and triacetin, titanium dioxide and stearic acid was added until all materials were well dispersed. The material was then sprayed onto the rotating tablet bed in the film coating device at a rate of 2 grams per minute with an atomizing pressure of 2 bars. Following the application of this enteric coat the tablets can be polished or a clear coat added for improved appearance.

EXAMPLE 4

Tablets containing 400 mg of AZT were prepared in the following manner.

| Ingredients | Amount (grams) |
| --- | --- |
| 1. Zidovudine (AZT) | 500 |
| 2. Dibasic Calcium Phosphate | 130 |
| 3. Lactose | 110 |
| 4. Cellulose Acetate Phthalate | 60 |
| 5. Triacetin | 8 |
| 6. Carbopol 934-P ® | 60 |
| 7. Methocel 4KM ® | 60 |
| 8. Hydrogenated Cotton Seed Oil | 70 |
| 9. Magnesium Stearate | 2 |

The AZT, lactose and dibasic calcium phosphate were screened through a number #20 mesh screen and blended in a fluid bed dryer at a temperature of 40° C. for 15 minutes. The cellulose acetate phthalate was dissolved in ammoniated deionized water with triacetin. The AZT along with lactose and dibasic calcium phosphate were granulated by spraying the polymer (CAP) under a pressure of 0.5–1 bar at a rate of 3 grams per minute while the material was fluidized at a temperature of 40° C. After the granulation was completed the granulate was further dried until the moisture content was less than 1%. The Methocel and Carbopol 934-P® were screened along with the magnesium stearate through a #20 mesh screen and blended with the granulated active agent. The granulate was then compressed on a tablet press to a weight of 800 mg±25 mg with a hardness of 10–15 kg.

EXAMPLE 5

Tablets weighing 800 mg and containing 125 mg of AZT and 187 mg of DDI are prepared in the following manner.

| Ingredients | Amount (grams) |
| --- | --- |
| 1. Zidovudine (AZT) | 156 |
| 2. 2',3' dideoxinosine (DDI) | 235 |
| 3. Dibasic Calcium Phosphate | 130 |
| 4. Anhydrous Lactose | 188 |
| 4. Cellulose Acetate Phthalate | 70 |
| 5. Triacetin | 8 |
| 6. Carbopol 934-P ® | 70 |

-continued

| Ingredients | Amount (grams) |
|---|---|
| 7. Methocel 4KM-P ® | 70 |
| 8. Hydrogenated Cotton Seed Oil | 70 |
| 9. Magnesium Stearate | 3 |

AZT, DDI, lactose and dibasic calcium phosphate are screened through a number #20 mesh screen and blended in a fluid bed dryer at a temperature of 40° C. for 15 minutes. The cellulose acetate phthalate is dissolved in ammoniated deionized water with triacetin. The AZT along with lactose and dibasic calcium phosphate are granulated by spraying the polymer (CAP) under a pressure of 0.5–1 bar at a rate of 3 grams per minute while the material is fluidized at a temperature of 40° C. After the granulation is complete the granulate is dried until the moisture content is less than 1%. The Methocel and Carbopol. 934-P® are screened along with the magnesium stearate through a #20 mesh screen and blended with the granulated active agent. The granulate is then compressed on a tablet press to a weight of 800 mg±25 mg with a hardness of 10–15 kg.

EXAMPLE 6

Tablets weighing 800 mg and containing 400 mg of AZT were prepared in the following manner.

| Ingredients | Amount (grams) |
|---|---|
| 1. Zidovudine (AZT) | 500 |
| 2. Dibasic Calcium Phosphate | 110 |
| 3. Microcrystalline Cellulose | 137 |
| 4. Anhydrous Lactose | 100 |
| 4. Ethyl Cellulose | 30 |
| 5. Carbopol 934-P ® | 40 |
| 6. Methocel 4KM-P ® | 40 |
| 7. Hydrogenated Cotton Seed Oil | 40 |
| 9. Magnesium Stearate | 3 |

AZT, dibasic calcium phosphate, microcrystalline cellulose, lactose, Carbopol 934-P, Methocel 4KM-P and hydrogenated cotton seed oil were passed through a number #20 mesh screen and placed in a fluid bed dryer. The products were heated and blended for 15 minutes at a temperature of 40° C. for fifteen minutes. Two hundred milliliters of pH 8.0 monophosphate buffer was slowly sprayed into the fluidizing bed at 0.5 bar of pressure and at a rate of 2 ml per minute using a Watson Marlow peristaltic pump. This produced a heavy granulation by entrapping the AZT into the polymerized Carbopol and Methocel. The granulate was dried until the moisture content was less than 2%. The granulate was removed and screened through an #18 mesh screen and returned to the fluid bed dryer. The ethyl cellulose was solvated with a Silverson mixer in 400 ml of anhydrous isopropyl alcohol. When the ethyl cellulose was completely dissolved it was sprayed into the fluidizing bed of granulated material at a rate of 2 ml per minute with an atomizing pressure of 1 bar and a heat of 40° C. After completion of the ethyl cellulose infusion the material was dried until the moisture content was less than 1%. The granulate was then milled through a #20 mesh screen and blended with the magnesium stearate. Tablets weighing 800 mg±40 mg with a fracture force strength of 15–20 kg were compressed on a 16 station rotary press. Strength being 10–15 kg.

EXAMPLE 7

The controlled-release of tablets produced by Example 1 were evaluated by dissolution of the tablets.

Six randomly selected tablets were evaluated by dissolution using a potassium monophosphate buffer (1000 ml of 0.05M $KH_2PO_4$) at pH 6.8 and with a paddle speed of 50 revolutions per minute, using a model 72 Hanson dissolution test station and a model 27 automated dissoette, as follows. Six round-bottom flasks were each filled with buffer and the temperature within each flask was maintained at 37°±0.5° C. The distance from the bottom of the paddle to the bottom of the flask was measured and adjusted to 2.5 cm, for each flask. Samples (4 ml) were drawn at 1,2,3,4,5,6,7, and 8 hours from each flask, and replaced with 4 ml of buffer. The percent of active drug release over time was analyzed by ultraviolet spectrophotometry (wavelength 268 nm) and high pressure liquid chromatography (HPLC).

A standard curve using serially diluted known quantities of AZT was first prepared for the HPLC analysis. An HPLC method was developed for the determination of AZT in standard was used for the quantitation. For AZT drug analysis and for dissolution sample analysis, the standard was prepared in 0.05M $KH_2PO_4$ at pH 6.8. Each sample or standard solution was then filtered through a 0.20 or a 0.45 micron filter for HPLC analysis. A C-18 column (Perkin Elmer) connected with an UV detector at 268 nm was used for the HPLC analysis. The mobile phase was potassuim monophosphate, pH 4.6 with 85% phosphoric acid/methanol (60/40, v/v) at a flow rate of 1.0 ml/min. The analysis time was 4–7 min/injection.

The dissolution results for these tablets produced by Example 1 are shown in Table 1.

TABLE 1

| DISSOLUTION OF AZT MADE FROM EXAMPLE 1 | | | | | | | | |
|---|---|---|---|---|---|---|---|---|
| HPLC READINGS | 1ST HOUR | 2ND HOUR | 3RD HOUR | 4TH HOUR | 5TH HOUR | 6TH HOUR | 7TH HOUR | 8TH HOUR |
| #1 ABS | 0.716 | 0.942 | 1.368 | 1.731 | 2.081 | 2.388 | 2.675 | 2.812 |
| CONC | 57 | 66 | 95 | 121 | 145 | 167 | 186 | 196 |
| PERCENT | 19.9 | 26.3 | 38.2 | 48.3 | 58 | 66.6 | 74.5 | 78.4 |
| #2 ABS | 0.617 | 1.055 | 1.508 | 1.925 | 2.309 | 2.623 | 2.919 | 3.100 |
| CONC | 43 | 74 | 105 | 134 | 161 | 184 | 203 | 216 |
| PERCENT | 17.2 | 29.4 | 42.1 | 53.7 | 64.4 | 73.2 | 81.4 | 86.7 |
| #3 ABS | 0.582 | 1.052 | 1.480 | 1.903 | 2.297 | 2.615 | 2.897 | 3.076 |
| CONC | 41 | 73 | 103 | 133 | 160 | 182 | 202 | 214 |
| PERCENT | 16.2 | 29.3 | 41.6 | 53.1 | 61.5 | 72.9 | 80.8 | 85.8 |
| #4 ABS | 0.554 | 1.005 | 1.435 | 1.834 | 2.206 | 2.540 | 2.838 | 3.038 |
| CONC | 39 | 70 | 100 | 128 | 154 | 177 | 197 | 212 |
| PERCENT | 15.4 | 28 | 39.9 | 51.1 | 61.5 | 70.8 | 79.1 | 84.7 |

TABLE 1-continued

DISSOLUTION OF AZT MADE FROM EXAMPLE 1

| HPLC READINGS | 1ST HOUR | 2ND HOUR | 3RD HOUR | 4TH HOUR | 5TH HOUR | 6TH HOUR | 7TH HOUR | 8TH HOUR |
|---|---|---|---|---|---|---|---|---|
| #5 ABS | 0.698 | 1.107 | 1.562 | 1.980 | 2.353 | 2.673 | 2.936 | 3.109 |
| CONC | 49 | 77 | 109 | 138 | 164 | 187 | 205 | 218 |
| PERCENT | 19.5 | 30.9 | 43.6 | 55.2 | 65.6 | 74.5 | 81.9 | 86.7 |
| #6 ABS | 0.576 | 0.996 | 1.410 | 1.794 | 2.140 | 2.442 | 2.649 | 2.947 |
| CONC | 40 | 69 | 98 | 125 | 149 | 170 | 184 | 205 |
| PERCENT | 16.1 | 27.8 | 39.3 | 50.0 | 59.7 | 68.1 | 73.9 | 82.2 |
| MEAN (%) | 17.4 | 28.6 | 40.7 | 51.9 | 61.8 | 71.0 | 78.6 | 84.1 |
| STD. DEV. | ±1.89 | ±1.59 | ±1.98 | ±2.56 | ±2.84 | ±3.12 | ±3.54 | ±3.22 |

TOTAL ASSAY: 101.5%
REGRESSION ANALYSIS OF MEAN PERCENTAGES, R = 0.994

This formulation demonstrated in vitro, linear release. More importantly the product when tested in human volunteers showed a prolonged low release rate when compared historically to the immediate release capsule formulation of AZT.

Table 2 shows the results of a random study using human volunteers and demonstrates the blood levels of zidovudine after a single dose to human volunteers of the product made by the process set forth in Example 1. In Table 2A, the subjects were given a single dose of a controlled release 250 mg tablet. In Table 2B, the subjects were given a single dose of two (2) controlled release 250 mg tablets (total 500 mg).

TABLE 2A

Blood AZT (zidovudine) Levels ng/mL
250 mg

| | 0 Hr. | 1 Hr. | 2 Hr. | 3 Hr. | 4 Hr. | 5 Hr. |
|---|---|---|---|---|---|---|
| SUB #2 | 0.00 | 63.00 | 96.00 | 88.00 | 96.00 | 67.00 |
| SUB #5 | 0.00 | 66.00 | 162.00 | 60.00 | 275.00 | 254.00 |
| SUB #11 | 0.00 | 122.00 | 118.00 | 122.00 | 67.00 | 45.00 |
| SUB #12 | 0.00 | 62.00 | 72.00 | 130.00 | 51.00 | 60.00 |
| SUB #8 | 0.00 | 66.00 | 162.00 | 118.00 | 375.00 | 231.00 |
| SUB #9 | 0.00 | 63.00 | 96.00 | 115.00 | 89.00 | 67.00 |
| Mean | 0.00 | 73.67 | 117.67 | 105.50 | 158.67 | 120.67 |

| | 6 Hr. | 7 Hr. | 8 Hr. | 9 Hr. | 10 Hr. | 11 Hr. | 12 Hr. |
|---|---|---|---|---|---|---|---|
| SUB #2 | 60.00 | 36.00 | 26.00 | 0.00 | 0.00 | 0.00 | 0.00 |
| SUB #5 | 117.00 | 57.00 | 36.00 | 28.00 | 27.00 | 0.00 | 0.00 |
| SUB #11 | 37.00 | 28.00 | 0.00 | 0.00 | 0.00 | 0.00 | 0.00 |
| SUB #12 | 42.00 | 34.00 | 42.00 | 35.00 | 44.00 | 41.00 | 0.00 |
| SUB #8 | 74.00 | 56.00 | 32.00 | 30.00 | 27.00 | 0.00 | 0.00 |
| SUB #9 | 60.00 | 35.00 | 28.00 | 31.00 | 28.00 | 0.00 | 0.00 |
| Mean | 65.00 | 40.83 | 27.33 | 20.67 | 21.00 | 6.83 | 0.00 |

TABLE 2B

Blood AZT (zidovudine) Levels ng/mL
500 mg

| | 0 Hr. | 1 Hr. | 2 Hr. | 3 Hr. | 4 Hr. | 5 Hr. |
|---|---|---|---|---|---|---|
| SUB #1 | 0.00 | 261.00 | 457.00 | 480.00 | 248.00 | 171.00 |
| SUB #3 | 0.00 | 163.00 | 325.00 | 298.00 | 214.00 | 238.00 |
| SUB #4 | 0.00 | 126.00 | 158.00 | 212.00 | 228.00 | 666.00 |
| SUB #6 | 0.00 | 131.00 | 125.00 | 150.00 | 112.00 | 91.00 |
| SUB #7 | 0.00 | 214.00 | 285.00 | 302.00 | 399.00 | 201.00 |
| SUB #10 | 0.00 | 250.00 | 321.00 | 116.00 | 118.00 | 110.00 |
| Mean | 0.00 | 192.33 | 278.67 | 261.33 | 219.50 | 249.50 |

TABLE 2B-continued

Blood AZT (zidovudine) Levels ng/mL
500 mg

| | 6 Hr. | 7 Hr. | 8 Hr. | 9 Hr. | 10 Hr. | 11 Hr. | 12 Hr. |
|---|---|---|---|---|---|---|---|
| SUB #1 | 127.00 | 69.00 | 59.00 | 35.00 | 36.00 | 0.00 | 0.00 |
| SUB #3 | 120.00 | 60.00 | 44.00 | 69.00 | 42.00 | 26.00 | 0.00 |
| SUB #4 | 331.00 | 165.00 | 91.00 | 60.00 | 51.00 | 57.00 | 36.00 |
| SUB #6 | 53.00 | 0.00 | 0.00 | 0.00 | 0.00 | 0.00 | 0.00 |
| SUB #7 | 118.00 | 80.00 | 65.00 | 65.00 | 0.00 | 0.00 | 0.00 |
| SUB #10 | 73.00 | 64.00 | 63.00 | 56.00 | 60.00 | 54.00 | 0.00 |
| Mean | 137.00 | 73.00 | 53.67 | 47.50 | 31.50 | 23.17 | 6.00 |

Figure 3:
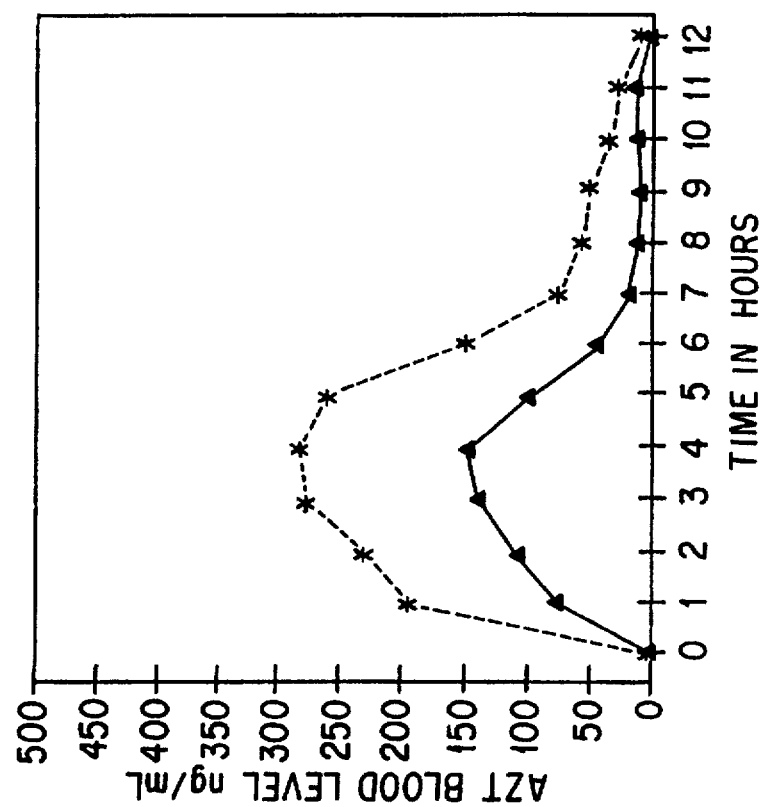
FIG. 3 is a graphic representation of dissolution blood levels from subjects given two strengths of controlled release AZT tablets.

Blood samples were taken from the volunteers every hour after dosing for 12 hours. After drawing the blood sample, the blood was allowed to clot and then centrifuged at 2000 rpm for 15 minutes. Following centrifugation the serum fraction was collected. All serum fractions were inactivated by heating at 56° C. for 120 minutes. The serum fraction samples were maintained at −20° C. Serum samples were assayed for AZT using a radio immunoassay. FIG. 3 is a graphic representation of blood levels from subjects given the 250 mg single dose and the two 250 mg (500 mg total) single dose over a 12 hour period.

EXAMPLE 8

In this example, the bioequivalence of the currently formulated AZT, sold under the product name Retrovir®, was compared with the controlled release formulation of this invention, named Aztec™. AZTEC® is a U.S. registered trademark of Verex Laboratories inc. As used herein, AZTEC® refers to the AZT controlled release tablets produced by the process set forth in Example 1. RETROVIR® is a U.S. registered trademark of Glaxo Wellcome and is a commercially available prescription of AZT, as described in the Physician's Desk Reference as 100 mg of AZT in capsule form. The comparison measured the pharmacokinetic profile of the formulations over time by assaying for phosphorylated, intracellular AZT and for blood serum levels of AZT.

The comparison was done as follows:

Each human volunteer subject was Given either Retrovir® 100 mg six times in 24 hours (600 mg/day) or Aztec™ 300 mg twice in 24 hours (600 mg/day). This dosage level continued for seven days when blood samples were evaluated and compared on sampling day seven. On the sample day, the AZT should have achieved a steady state of concentration. At time zero on the sampling day, the final dose was given. For those patients receiving Retrovir®, 100 mg of AZT was Given; for those subjects receiving Aztec™, 300 mg of AZT was given. At day seven blood samples were drawn at 0, 1, 2, 3, 4, 5, 6, 7, 8, 10, 12, 16, and 24 hours for patients receiving Aztec™, while blood samples were drawn at 0, 0.5, 1.0, 1.5, 2.0, 2.5, 3.0, 3.5, 4, 5, 6.5, 8, and 24 hours in patients receiving Retrovir®. The reason for the different time sampling was to more accurately reflect AZT levels since the Retrovir® formulation immediately releases AZT and Aztec™ releases AZT at a controlled rate.

Blood samples drawn at 0, 2, 4, 8, and 24 hours were used in assaying for intracellular phosphorylated AZT. Blood samples drawn every hour up to twelve hours were used in assaying blood serum AZT. Fifteen milliliters of blood was drawn at each time interval using a red top Vacutainer®.

The samples were allowed to clot. After clotting, the samples were then centrifuged at 2000 rpm for 15 minutes and the serum fraction collected. The specimen was placed in an appropriate borosilicate tube with screw cap and refrigerated at 0°–10° C. All serum samples were inactivated by heating at +56° C. for 120 minutes, and then they were maintained at −20° C.

Serum samples for AZT were assayed for blood serum levels and for phosphorylated AZT using the following radioimmunoassay method and as described in Stretcher, B. N., *Therapeutic Drug Monitor,* 12(5) (1990), (Stretcher, B. N. et al., *Clin. Pharmacol. Ther.,* 49:198 (1992) and Stretcher, B. N. et al., *Clin. Pharmacol. Ther.,* 49:182 (1992)).

1. Ten milliliter blood samples were drawn at 0, 4, 8 and 24 hours on the study day. Mononucleocytes were isolated using Ficoil-Hypaque.
2. Cells were washed and extracted for 12 hours with 60% methanol.
3. The cell extract was evaporated to dryness, then reconstituted in pH 9.5 Tris/MgCl$_2$, then split into equal fractions.
4. The first fraction was treated with 0.5 mg/ml alkaline phosphatase which removes the 5'-phosphate groups.
5. Both fractions were then assayed for AZT using a sensitive and specific radio immunoassay method set forth in Stretcher, B. N., *Therapeutic Drug Monitor,* 12(5) (1990).
6. Assayed concentrations of phosphorylated AZT were calculated by difference and intracellular concentrations were calculated by correcting for assay volume and the number of cells.

Figure 4:
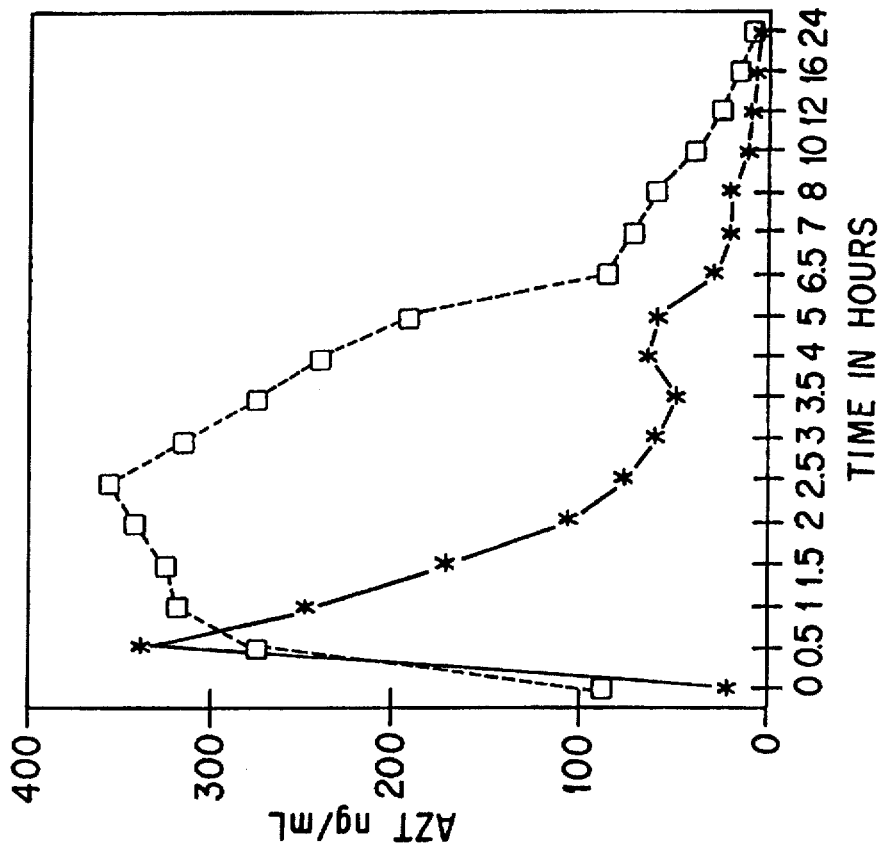
FIG. 4 is a graph showing the comparative levels of steady state mean serum blood concentration levels of AZT between subjects receiving Aztec™ and subjects receiving Retrovir®.

FIG. 4 is graphic representation comparing the steady state mean serum blood concentration levels between Retrovir® and Aztec™. Table 3 sets forth serum concentration levels of AZT over time at steady state day 7 in patients given either Aztec™ (Table 3A) or Retrovir® (Table 3B). This graph shows that following oral administration, AZT passes into the intestine, where it is released from the dosage form, eventually dissolves, and is absorbed. As the sampling and analysis continued, the blood samples revealed increasing concentrations of the drug until the maximum (peak) concentration was reached. Then, the blood level of the drug progressively decreased, and eventually falls. The diminished blood level of AZT after the peak height was reached indicates that the rate of drug elimination from the blood stream was greater than the rate of drug absorption into the circulatory system. The goal is to avoid high peak areas after the final dose is given.

TABLE 3A

SERUM LEVELS OF AZT (zidovudine) ng/mL
AZTEC ® 300 mg STEADY STATE DAY 7

| Pt # | 0 H | 1 H | 2 H | 3 H | 4 H | 5 H | 6 H | 7 H | 8 H | 10 H | 12 H | 16 H | 24 H |
|---|---|---|---|---|---|---|---|---|---|---|---|---|---|
| 1 | 122.2 | 841.2 | 644.1 | 533.8 | 360.6 | 239.0 | 92.4 | 47.5 | 36.5 | 11.8 | 24.6 | 7.5 | 7.2 |
| 2 | 36.9 | 250.3 | 313.3 | 319.5 | 282.1 | 146.7 | 91.3 | 50.3 | 43.2 | 20.6 | 18.1 | 10.3 | 8.4 |
| 3 | 23.3 | 111.4 | 156.3 | 114.2 | 113.7 | 79.9 | 69.9 | 42.5 | 24.2 | 29.5 | 8.0 | 23.4 | 2.1 |
| 5 | 51.0 | 188.0 | 192.2 | 139.9 | 140.6 | 175.9 | 93.2 | 81.9 | 58.9 | 50.5 | 30.2 | 16.1 | 6.4 |
| 6 | 39.9 | 232.6 | 264.4 | 302.0 | 246.0 | 197.0 | 169.8 | 64.9 | 46.9 | 29.2 | 14.5 | 11.9 | 5.4 |
| 7 | 46.2 | 152.6 | 208.2 | 323.5 | 301.7 | 256.5 | 96.7 | 69.7 | 66.7 | 59.6 | 28.0 | 18.7 | 9.2 |
| 8 | 61.9 | 321.6 | 439.0 | 312.4 | 190.9 | 243.1 | 60.4 | 160.4 | 149.6 | 83.8 | 53.5 | 31.5 | 18.9 |
| 9 | 321.2 | 451.5 | 516.1 | 471.7 | 275.6 | 189.6 | 108.2 | 57.0 | 51.1 | 28.1 | 25.6 | 9.6 | 7.9 |
| 10 | 13.0 | 256.0 | 294.6 | 350.6 | 321.1 | 265.4 | 122.9 | 69.1 | 55.9 | 26.2 | 40.6 | 24.1 | 3.5 |
| 11 | 16.1 | 85.5 | 155.6 | 113.2 | 201.5 | 143.6 | 79.4 | 95.9 | 69.8 | 37.5 | 37.8 | 12.1 | 10.0 |
| 12 | 163.7 | 330.1 | 265.9 | 279.5 | 182.6 | 90.2 | 66.1 | 28.9 | 21.7 | 26.8 | 15.2 | 15.5 | 2.0 |
| Mean | 81.4 | 292.8 | 313.6 | 296.4 | 237.9 | 184.3 | 95.5 | 69.8 | 56.8 | 36.7 | 26.9 | 16.4 | 7.4 |
| SD± | 91.9 | 210.1 | 157.0 | 135.3 | 78.1 | 64.3 | 30.8 | 35.4 | 34.5 | 20.5 | 13.3 | 7.4 | 4.7 |
| SEM± | 27.7 | 63.3 | 47.3 | 40.8 | 23.5 | 19.4 | 9.3 | 10.7 | 10.4 | 6.2 | 4.0 | 2.2 | 1.4 |

TABLE 3B

SERUM LEVELS OF AZT (zidovudine) ng/mL
RETROVIR ® 100 mg STEADY STATE DAY 7

| Pt # | 0 H | 0.5 H | 1 H | 1.5 H | 2 H | 2.5 H | 3 H | 3.5 H | 4 H | 5 H | 6.5 H | 8 H | 24 H |
|---|---|---|---|---|---|---|---|---|---|---|---|---|---|
| 1 | 10.2 | 6.1 | 4.2 | 4.7 | 7.4 | 6.0 | 16.3 | 38.9 | 148.9 | 212.6 | 74.1 | 37.0 | 2.6 |
| 2 | 4.8 | 552.4 | 232.7 | 193.0 | 105.0 | 101.4 | 67.2 | 36.3 | 35.3 | 20.4 | 16.8 | 8.8 | 0 |
| 3 | 23.8 | 498.9 | 294.9 | 172.5 | 138.7 | 103.9 | 84.0 | 67.1 | 62.8 | 41.0 | 25.3 | 25.1 | 6.7 |
| 5 | 48.0 | 118.9 | 416.3 | 186.7 | 110.0 | 59.3 | 41.8 | 33.8 | 41.6 | 37.4 | 23.2 | 16.5 | 6.0 |
| 6 | 8.6 | 69.2 | 249.0 | 226.7 | 120.5 | 77.1 | 54.4 | 36.5 | 37.2 | 32.7 | 15.5 | 9.1 | 9.4 |
| 7 | 17.3 | 136.2 | 244.2 | 200.7 | 158.1 | 89.8 | 80.2 | 61.0 | 58.7 | 33.9 | 19.9 | 17.8 | 7.3 |
| 8 | 28.2 | 590.9 | 259.9 | 159.1 | 138.9 | 115.8 | 84.2 | 77.2 | 78.7 | 54.5 | 31.5 | 24.6 | 12.0 |
| 9 | 38.0 | 735.6 | 265.5 | 224.8 | 65.9 | 50.5 | 40.6 | 37.4 | 43.0 | 41.3 | 18.6 | 13.5 | 4.6 |
| 10 | 0.7 | 349.6 | 136.2 | 152.2 | 329.6 | 90.8 | 58.7 | 63.9 | 47.3 | 20.5 | 18.5 | 17.6 | 4.3 |
| 11 | 17.8 | 569.9 | 202.3 | 155.7 | 131.2 | 97.2 | 79.8 | 34.4 | 24.5 | 27.0 | 14.9 | 10.1 | 5.7 |
| 12 | 16.0 | 405.8 | 193.8 | 86.1 | 71.3 | 36.0 | 32.7 | 18.6 | 28.4 | 21.0 | 9.2 | 5.0 | 0 |
| Mean | 19.4 | 366.7 | 227.2 | 160.2 | 125.1 | 75.3 | 58.2 | 45.9 | 55.1 | 49.3 | 29.3 | 16.8 | 5.3 |
| SD± | 14.3 | 247.9 | 101.7 | 64.7 | 80.2 | 33.6 | 23.2 | 18.2 | 34.9 | 55.2 | 17.5 | 9.3 | 3.7 |
| SEM± | 4.3 | 74.7 | 30.7 | 19.5 | 24.2 | 10.1 | 7.0 | 5.5 | 10.5 | 16.6 | 5.3 | 2.8 | 1.1 |

Figure 5:
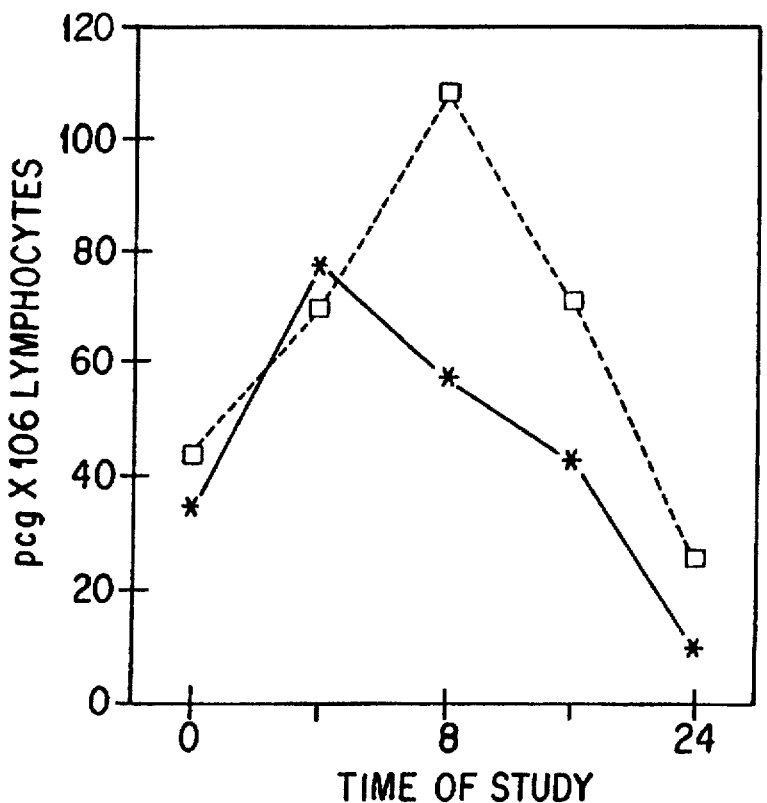
FIG. 5 is a graph showing the comparative levels of intracellular phosphorylated AZT between subjects receiving controlled release Aztec™ and subjects receiving Retrovir®.

Table 4 sets forth the intracellular phosphorylated AZT levels in patients given either Aztec™ (Table 4A) or Retrovir® (Table 4B). The results are compared in FIG. 5 in which the resulting data was plotted to yield the intracellular phosphorylation of AZT concentration curve. The vertical axis presents the concentration of AZT present in the blood cells and the horizontal axis presents the time the samples were obtained following the administration of the drug. The data shows that that the intracellular level of phosphorylated AZT had a higher desired therapeutic level intracellularly and a gradual release of additional amounts of drug to maintain this desired therapeutic level of effect over the 24 hour testing period. The results from this comparison shows that the controlled release formulation achieves the goal of reduction in drug blood level fluctuations, reduction in dosing frequency, reduction in adverse side effects, as well as enhanced patient convenience and compliance.

It is noted that Table 3 presents serum levels of AZT for 11 patients while Table 4 presents intracellular phosphorylated AZT levels for 12 patients. This difference is because the FDA stopped the study after 12 patients had completed it, but blood levels were run on only 11 of these patients.

TABLE 4A

AZTEC ® pcg/10⁶ MONOCYTES
INTRACELLULAR PHOSPHORYLATED AZT

| PATIENT | 0 HR | 2 HR | 4 HR | 8 HR | 24 HR |
|---|---|---|---|---|---|
| 1 | 48.46 | 89.73 | 68.27 | 77.18 | 57.77 |
| 2 | 0.07 | 18.70 | 15.44 | 13.01 | 0 |
| 3 | 10.76 | 23.11 | 210.8 | 116.4 | 56.91 |
| 5 | 9.01 | 31.77 | 66.76 | 60.94 | 0.56 |
| 6 | 70.72 | 86.78 | 161.5 | 90.56 | 17.68 |
| 7 | 69.05 | 54.26 | 43.65 | 37.62 | 2.49 |
| 8 | 24.92 | 45.59 | 63.61 | 35.19 | 40.56 |
| 9 | 117.2 | 203.2 | 234.3 | 134.9 | 31.84 |
| 10 | 1.78 | 73.09 | 57.58 | 68.69 | 36.62 |
| 11 | 13.90 | 26.61 | 28.85 | 26.54 | 0.79 |
| 12 | 27.30 | 12.28 | 33.63 | 56.29 | 10.38 |
| 13 | 12.82 | 63.93 | 76.72 | 16.68 | 9.67 |
| MEAN | 33.83 | 60.75 | 88.43 | 61.17 | 22.11 |
| SD± | 35.73 | 52.03 | 72.65 | 38.63 | 21.81 |
| SEM± | 10.31 | 15.02 | 20.97 | 11.15 | 6.30 |

TABLE 4B

RETROVIR ® pcg/10⁶ MONOCYTES
INTRACELLULAR PHOSPHORYLATED AZT

| PATIENT | 0 HR | 2 HR | 4 HR | 8 HR | 24 HR |
|---|---|---|---|---|---|
| 1 | 5.65 | 18.35 | 20.65 | 51.55 | 13.08 |
| 2 | 0.30 | 9.80 | 7.26 | 12.08 | 12.40 |
| 3 | 22.39 | 95.54 | 86.18 | 82.26 | 0 |
| 5 | 7.48 | 32.85 | 7.40 | 15.63 | 13.06 |
| 6 | 30.38 | 190.13 | 34.05 | 24.19 | 0 |
| 7 | 45.47 | 186.39 | 49.25 | 35.37 | 22.59 |
| 8 | 5.55 | 5.46 | 10.39 | 14.09 | 0 |
| 9 | 16.03 | 71.56 | 237.3 | 105.3 | 13.91 |
| 10 | 25.41 | 30.50 | 16.31 | 18.18 | 9.76 |
| 11 | 12.15 | 26.49 | 29.46 | 6.60 | 18.55 |
| 12 | 6.71 | 24.29 | 78.47 | 17.08 | 5.12 |
| 13 | 3.76 | 93.29 | 75.94 | 72.44 | 17.33 |
| MEAN | 15.11 | 65.39 | 54.39 | 37.90 | 10.48 |
| SD± | 13.42 | 64.88 | 64.33 | 32.60 | 7.67 |
| SEM± | 3.87 | 18.73 | 18.57 | 9.38 | 2.21 |

EXAMPLE 9

In this example, the serum zidovudine levels produced with Aztec™ at equal dosages, before and after a fatty meal were s compared to determine the effect of food on the rate and extent of drug absorption. Retrovir®, the currently available formulation of AZT, is known to have a marked food drug interaction with significant lowering of the amount and extent of drug absorbed when the product is administered with food (>50% decrease in AZT bioavailability when Retrovir® is taken with food) (Lotterer, E., et al., *Eur. J. Clin. Pharmacol.*, 40(3):305–308 (1991)).

Twelve healthy male subjects were selected for the comparison. The subjects were between 18–40 years of age and were at their ideal weight for height and frame, plus or minus 15%. Prior to the comparison, each subject was given a complete physical exam. Further, a clinical laboratory profile was obtained for each subject. The resultant laboratory values were within clinically acceptable limits for each subject.

The comparison was carried out as a single-dose, open-label, two-way crossover design with each of the twelve subjects receiving one 300 mg tablet of Aztec™ fasting and one 300 mg tablet immediately after a high fat breakfast. Subjects were randomized to receive the drug either fasting or non-fasting and then were crossed over to the alternate state. There was a seven day washout period between each dose. Subjects remained housed for 12 hours before each dose and for 24 hours total time, from entry until discharge.

The subjects reported to the study unit on the evening prior to each dose day and remained housed for 24 hours. The diet pattern was as follows on each of the two dose days: (a) no coffee, tea, alcohol or chocolate allowed during the study; (b) subjects who received medication in the non-fasting state, within 15 minutes prior to dosing, ingest the following standard high fat meal: two fried eggs, two strips of bacon, two pieces of buttered toast, and 8 oz. of whole milk; (c) at four hours after dosing all subjects resumed the regular house diet; and (d) water was taken ad libitum.

At dosing time on each of the two dose days subjects ingested a single 300 mg tablet of Aztec™ with 180 ml of water. See Table 5 below for the dosing schedule. Serum samples for zidovudine were obtained at 0 hours pre-dose, 1, 2, 3, 4, 5, 6, 7, 8, 9, 10, 11, and 12 hours post-dose. Each dose day was separated by a washout period of seven days. Prior to discharge from the study a physical examination and clinical laboratory profile was repeated for each subject. No clinically significant physical findings were observed.

TABLE 5

| Subject Number | Dose 1 | Dose 2 |
| --- | --- | --- |
| 1 | A | B |
| 2 | A | B |
| 3 | B | A |
| 4 | B | A |
| 5 | B | A |
| 6 | A | B |
| 7 | B | A |
| 8 | B | A |
| 9 | A | B |
| 10 | A | B |
| 11 | B | A |
| 12 | A | B |

A = Aztec ™ 300 mg given after an 8 hour fast.
B = Aztec ™ 300 mg given within 15 minutes after a high fat breakfast.

Serum samples were assayed for AZT using a sensitive and specific radioimmunoassay method (Stretcher, B. N., *Therapeutic Drug Monitor*, 12(5) (1990)). Because of the possibility of a sequence effect, the data was analyzed in each arm of the study (12 subjects per group, paired t-test), with a 90% chance of detecting similar sized differences at the $p \leq 0.05$ probability level. Twelve patients per group also gives a 50% chance of detecting a difference in the maximum plasma AZT concentrations 0.05 level and a 99% chance of detecting a difference in the plasma AZT half life at the $p \leq 0.01$ level of significance. The frequency of side effects and/or laboratory abnormalities were compared by the Chi squared or non-parametric tests. The pharmacokinetic data was calculated by ANOVA to determine if there are any statistically significant (p<0.005) differences between dosing groups. A ratio analysis was performed for individual subject's pharmacokinetic data as well as a mean plot of the data.

Throughout the study subjects were questioned using an indirect technique to determine any adverse side effects. Such effects were graded as follows: none; mild; moderate; or severe. Subjects 2–4, 6–7, and 9–12 exhibited no adverse side effects. No subjects experienced side effects during the fatty meal portion of the study. During the fasting portion of the study subject #1 experienced mild nausea and vomiting which was possibly drug related. Subject #5 experienced a mild headache during the fasting portion of the study which was not drug related (the headache resolved after lunch). Subject #8 experienced mild nausea during the fasting portion of the study which resolved after lunch and was not drug related.

Table 6 sets forth serum levels of AZT over time in fasted and fed subjects. In Table 6A subjects were given a 300 mg Aztec™ tablet after fasting. In Table 6B subjects were given a 300 mg Aztec™ tablet after ingesting a fatty meal. Blood samples were drawn, processed and assayed for AZT as set forth in example 8 above.

TABLE 6A

SERUM LEVELS OF AZT (zidovudine) ng/mL
AZTEC ® 300 mg FASTING
IND # 40,804 PROTOCOL VX 93-01

| Pt # | 0 H | 1 H | 2 H | 3 H | 4 H | 5 H | 6 H | 7 H | 8 H | 9 H | 10 H | 11 H | 12 H |
| --- | --- | --- | --- | --- | --- | --- | --- | --- | --- | --- | --- | --- | --- |
| 1 | 0 | 87.8 | 111.8 | 171.9 | 141.0 | 53.8 | 30.8 | 21.5 | 14.0 | 5.1 | 8.8 | 13.5 | 9.5 |
| 2 | 0 | 63.2 | 119.4 | 342.6 | 206.6 | 129.5 | 57.8 | 29.7 | 16.4 | 17.8 | 34.5 | 15.5 | 21.7 |
| 3 | 0 | 150.9 | 264.0 | 295.3 | 171.5 | 121.4 | 90.9 | 34.9 | 14.1 | 10.1 | 6.0 | 2.9 | 1.6 |
| 4 | 0 | 87.4 | 170.3 | 72.6 | 244.5 | 132.4 | 18.1 | 13.5 | 7.0 | 13.9 | 8.0 | 2.6 | 1.1 |
| 5 | 0 | 319.8 | 337.1 | 357.9 | 243.5 | 133.2 | 76.7 | 48.4 | 29.6 | 23.9 | 18.0 | 14.4 | 9.4 |
| 6 | 0 | 45.1 | 59.0 | 44.0 | 39.5 | 46.4 | 27.5 | 56.6 | 89.1 | 37.3 | 52.9 | 31.5 | 92.8 |
| 7 | 0 | 248.5 | 424.1 | 319.4 | 423.4 | 385.5 | 203.5 | 54.0 | 33.6 | 55.3 | 27.6 | 31.6 | 19.3 |
| 8 | 0.16 | 224.4 | 353.4 | 344.0 | 293.6 | 195.7 | 168.8 | 125.6 | 68.8 | 57.8 | 16.6 | 10.8 | 8.8 |
| 9 | 2.5 | 144.7 | 223.0 | 93.6 | 193.3 | 123.2 | 110.1 | 21.9 | 12.4 | 21.8 | 16.4 | 11.8 | 9.9 |
| 10 | 0 | 118.0 | 239.6 | 178.5 | 105.3 | 56.8 | 56.6 | 25.1 | 35.9 | 18.3 | 10.3 | 10.5 | 5.4 |
| 11 | 0 | 183.9 | 403.7 | 344.4 | 485.6 | 310.3 | 230.3 | 66.7 | 55.6 | 32.9 | 17.4 | 7.1 | 9.5 |
| 12 | 0 | 115.1 | 144.9 | 139.9 | 71.2 | 43.1 | 19.3 | 23.6 | 17.3 | 16.3 | 53.4 | 22.6 | 10.4 |
| Mean | 0 | 149.1 | 237.5 | 225.3 | 218.3 | 144.3 | 90.9 | 43.5 | 32.8 | 25.9 | 22.5 | 14.6 | 16.6 |
| SD± | 0 | 81.9 | 121.1 | 120.3 | 133.4 | 106.8 | 73.3 | 30.8 | 25.8 | 16.8 | 16.5 | 9.8 | 24.7 |
| SEM± | 0 | 23.6 | 35.0 | 34.7 | 38.5 | 30.8 | 21.2 | 8.4 | 7.4 | 4.9 | 4.8 | 2.8 | 7.1 |

$AUC_{0-24}$
Subject #1 664.8 ng · mL/hr
Subject #2 1043.3 ng · mL/hr
Subject #3 1162.8 ng · mL/hr
Subject #4 770.9 ng · mL/hr
Subject #5 1607.2 ng · mL/hr

TABLE 6A-continued

SERUM LEVELS OF AZT (zidovudine) ng/mL
AZTEC ® 300 mg FASTING
IND # 40,804 PROTOCOL VX 93-01

| Pt # | 0 H | 1 H | 2 H | 3 H | 4 H | 5 H | 6 H | 7 H | 8 H | 9 H | 10 H | 11 H | 12 H |
|---|---|---|---|---|---|---|---|---|---|---|---|---|---|

Subject #6 575.3 ng · mL/hr
Subject #7 2216.2 ng · mL/hr
Subject #8 1863.9 ng · mL/hr
Subject #9 977.3 ng · mL/hr
Subject #10 857.6 ng · mL/hr
Subject #11 2142.7 ng · mL/hr
Subject #12 671.9 ng · mL/hr

TABLE 6B

SERUM LEVELS OF AZT (zidovudine) ng/mL
AZTEC ® 300 mg FOLLOWING FATTY MEAL
IND # 40,804 PROTOCOL VX 93-01

| Pt # | 0 H | 1 H | 2 H | 3 H | 4 H | 5 H | 6 H | 7 H | 8 H | 9 H | 10 H | 11 H | 12 H |
|---|---|---|---|---|---|---|---|---|---|---|---|---|---|
| 1 | 0 | 59.4 | 130.0 | 158.2 | 170.7 | 346.6 | 219.9 | 83.8 | 67.0 | 33.8 | 18.3 | 8.0 | 4.5 |
| 2 | 0 | 31.4 | 118.6 | 162.1 | 384.5 | 267.5 | 147.5 | 64.1 | 25.7 | 14.4 | 9.8 | 3.8 | 2.6 |
| 3 | 0 | 35.8 | 78.5 | 120.5 | 275.5 | 314.1 | 230.1 | 148.9 | 102.8 | 89.8 | 170.6 | 77.6 | 39.9 |
| 4 | 0 | 90.1 | 130.4 | 101.8 | 188.6 | 574.6 | 199.6 | 67.1 | 25.5 | 21.5 | 11.0 | 4.4 | 4.3 |
| 5 | 0 | 246.5 | 346.4 | 304.5 | 238.5 | 269.0 | 222.1 | 189.2 | 172.7 | 102.1 | 47.6 | 28.2 | 10.8 |
| 6 | 0 | 11.8 | 9.5 | 6.8 | 69.9 | 156.9 | 49.7 | 27.3 | 22.6 | 33.9 | 60.1 | 155.3 | 141.4 |
| 7 | 0 | 116.0 | 672.7 | 694.4 | 469.4 | 133.8 | 75.1 | 28.3 | 27.6 | 31.0 | 14.1 | 30.4 | 20.8 |
| 8 | 0 | 147.8 | 147.5 | 120.1 | 333.3 | 500.3 | 298.6 | 170.4 | 88.5 | 35.1 | 26.6 | 9.8 | 7.8 |
| 9 | 0 | 4.6 | 33.7 | 115.4 | 179.3 | 198.8 | 290.2 | 235.5 | 171.8 | 142.4 | 116.1 | 77.7 | 53.3 |
| 10 | 0 | 34.6 | 108.1 | 250.2 | 458.8 | 464.7 | 195.2 | 96.8 | 45.9 | 30.5 | 20.2 | 15.7 | 11.4 |
| 11 | 0 | 50.9 | 133.6 | 175.7 | 192.7 | 292.6 | 188.3 | 92.1 | 69.6 | 77.8 | 54.0 | 73.7 | 82.8 |
| 12 | 0 | 149.2 | 133.9 | 221.0 | 222.9 | 144.7 | 71.3 | 26.0 | 95.3 | 93.0 | 61.9 | 21.9 | 20.3 |
| Mean | 0 | 81.5 | 170.2 | 202.6 | 265.3 | 305.3 | 182.3 | 102.5 | 76.3 | 58.8 | 50.9 | 42.2 | 33.3 |
| SD± | 0 | 71.6 | 178.8 | 172.9 | 122.9 | 144.4 | 81.8 | 68.9 | 53.2 | 40.6 | 48.7 | 45.6 | 41.7 |
| SEM± | 0 | 20.7 | 51.4 | 49.9 | 35.5 | 41.7 | 23.6 | 19.9 | 15.3 | 11.7 | 14.0 | 13.2 | 12.0 |

Figure 6:
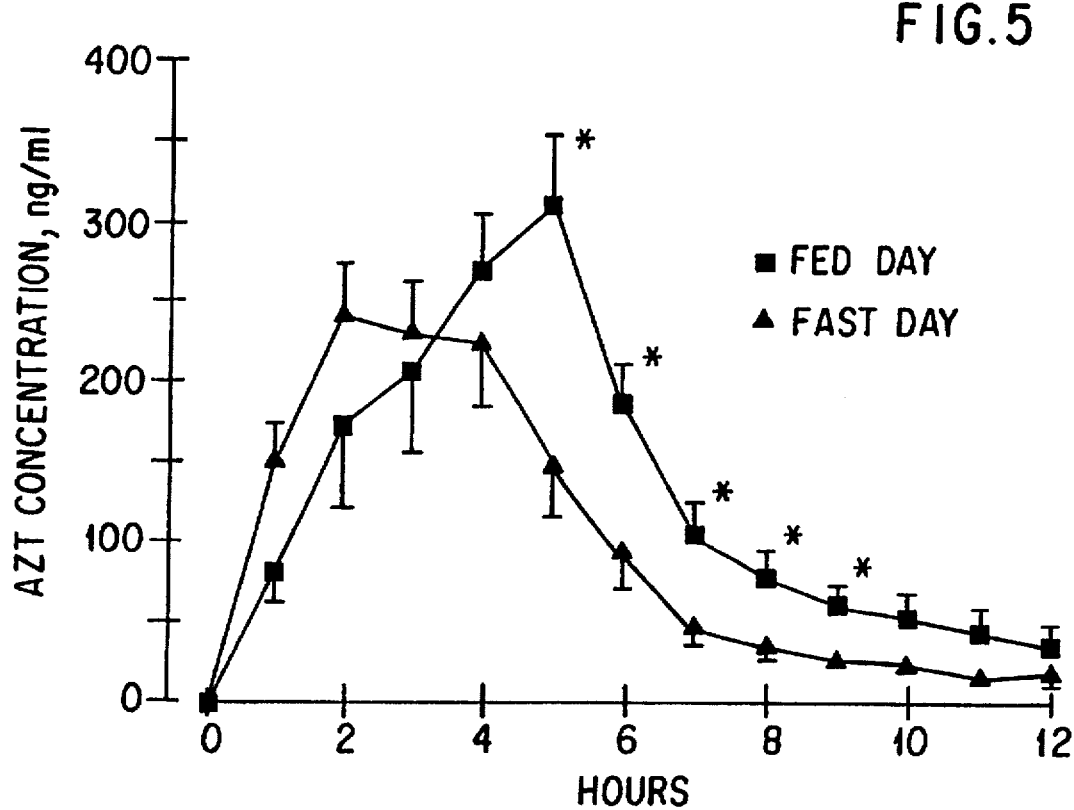
FIG. 6 is a graph showing a comparison of mean serum AZT levels in subjects who received Aztec™ after fasting and subjects who received Aztec™ after ingesting a fatty meal.

$AUC_{0-24}$
Subject #1 1298.0 ng · mL/hr
Subject #2 1230.7 ng · mL/hr
Subject #3 1664.2 ng · mL/hr
Subject #4 1416.8 ng · mL/hr
Subject #5 2172.2 ng · mL/hr
Subject #6 674.5 ng · mL/hr
Subject #7 2303.7 ng · mL/hr
Subject #8 1881.9 ng · mL/hr
Subject #9 1592.2 ng · mL/hr
Subject #10 1726.4 ng · mL/hr
Subject #11 1443.5 ng · mL/hr
Subject #12 1251.7 ng · mL/hr The results of this comparison are shown in FIG. 6 in which the resulting data from Table 6 was plotted to yield the effect of food on serum AZT levels with Aztec™ curve. The vertical axis presents the mean concentration of AZT present in the serum and the horizontal axis presents the time the samples were obtained before (0 hours) and following (1–12 hours) the administration of the drug. The data shows that when Aztec™ is taken after a fatty meal, there is no significant reduction in the blood levels of AZT. These results indicate that with Aztec™, there is no food-drug interaction or inhibition of AZT absorption in association with food.

EXAMPLE 10

In this example, steady state serum levels of AMT (AZT's catabolite) were compared in subjects receiving the present controlled release formulation Aztec™ and the currently available formulation Retrovir®, at equal dosages per day. The comparison measured serum levels of AMT over time. The comparison was done as set forth below.

Male and nonpregnant female subjects were selected for the comparison. The subjects were between 18–60 years of age and were HIV positive as demonstrated by enzyme linked immunosorbent assay with confirmation by Western blot or other type of confirmation. The subjects had a Karnofsky performance status of >70% (the subject is at least able to care for himself but may be unable to carry on normal activity or to do active work) and did not suffer from any life threatening opportunistic infection. Prior to the comparison, each subject was given a complete physical exam. Further, a clinical laboratory profile was obtained for each subject. The resultant laboratory values were within clinically acceptable limits for patients with HIV, for each subject.

The comparison was carried out as an open-label, multiple-dose, steady-state, two-way crossover design. Each subject received, in a randomized fashion, a 300 mg tablet of Aztec™ twice daily at 08:00 hours and at 20:00 hours, a 100 mg capsule of Retrovir® six times daily one capsule every three hours while awake. See Table 7 below for the randomization schedule for drug assignment. Each treatment period was for seven days duration, with no washout period between crossovers. Subjects were treated as outpatients. During the last 24 hours of each study period the subjects were housed for drawing of blood samples.

TABLE 7

| Patient Number | Group A | Group B |
|---|---|---|
| 1 | R | A |
| 2 | A | R |
| 3 | A | R |
| 5 | R | A |

All patients were numbered sequentially as they entered the study. They started out as Group A and received either Aztec™ (A) or Retrovir® (R) during their first treatment period of seven days. All patients were then assigned to Group B for the remainder of the study period and received the medication as shown in the above schedule.

according to the procedure set forth in example 8 above. Serum samples were assayed for AMT using a modification of the method set forth in Stagg, P. M. et al., *Clin. Pharmacol. Ther.*, 51:668–676 (1992).

Figure 7:
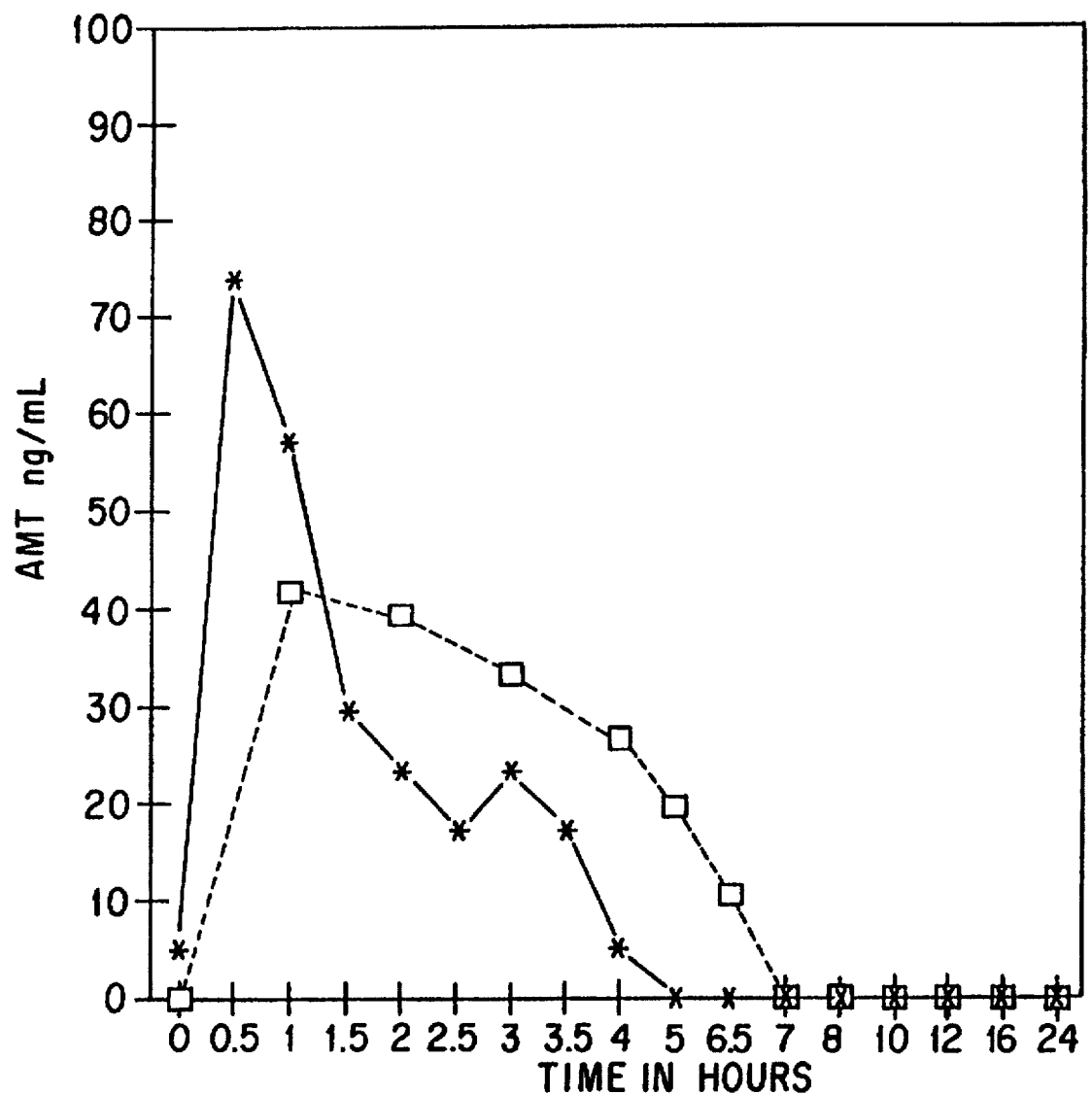
FIG. 7 is a graph showing a comparison of the steady state mean serum levels of AMT in subjects given either Aztec™ or Retrovir®.

Table 8 sets forth serum levels of AMT over time at steady state day 7 in patients given either Aztec™ (Table 8A) or Retrovir® (Table 8B). FIG. 7 is a graphic representation of serum levels of AMT in subjects given either Aztec™ containing 300 mgs of AZT per dosage unit or Retrovir® containing 100 mgs of AZT per dosage unit. The obtained data shows that the present controlled release formulation achieves the goal of reducing the amount of AMT produced.

TABLE 8A

SERUM LEVELS OF AMT (zidovudine) ng/mL
AZTEC ® 300 mg STEADY STATE DAY 7
IND # 40,804 PROTOCOL VX 92-3
First Four Patients-Levels Below 10 ng/mL Are Non Detectable And Are Marked As Such

| Pt # | 0 H | 1 H | 2 H | 3 H | 4 H | 5 H | 6 H | 7 H | 8 H | 10 H | 12 H | 16 H | 24 H |
|---|---|---|---|---|---|---|---|---|---|---|---|---|---|
| 1 | 14.7 | 100.9 | 77.3 | 64.1 | 43.3 | 28.7 | 11.1 | ND | ND | ND | ND | ND | ND |
| 2 | ND | 30.0 | 37.6 | 38.3 | 33.9 | 17.6 | 11.0 | ND | ND | ND | ND | ND | ND |
| 3 | ND | 13.4 | 18.8 | 13.7 | 13.6 | 10.0 | ND | ND | ND | ND | ND | ND | ND |
| 5 | ND | 22.6 | 23.1 | 16.8 | 16.8 | 21.1 | 11.2 | ND | ND | ND | ND | ND | ND |
| Mean | ND | 41.7 | 39.2 | 33.2 | 26.9 | 19.3 | 10.4 | ND | ND | ND | ND | ND | ND |

TABLE 8B

SERUM LEVELS OF AMT (zidovudine) ng/mL
RETROVIR ® 100 mg STEADY STATE DAY 7
IND # 40,804 PROTOCOL VX 92-3
First Four Patients-Levels Below 10 ng/mL Are Non Detectable And Are Marked As Such

| Pt # | 0 H | 0.5 H | 1 H | 1.5 H | 2 H | 2.5 H | 3 H | 3.5 H | 4 H | 5 H | 6.5 H | 8 H | 24 H |
|---|---|---|---|---|---|---|---|---|---|---|---|---|---|
| 1 | ND | ND | ND | ND | ND | ND | 37.2 | 53.2 | 18.5 | ND | ND | ND | ND |
| 2 | ND | 138.1 | 48.3 | 26.3 | 25.4 | 16.8 | ND | ND | ND | ND | ND | ND | ND |
| 3 | ND | 124.7 | 73.7 | 43.1 | 34.7 | 26.0 | 21 | 16.8 | ND | ND | ND | ND | ND |
| 5 | 12.0 | 29.7 | 104.8 | 46.7 | 27.5 | 14.8 | 10.5 | ND | ND | ND | ND | ND | ND |
| Mean | 5.43 | 73.5 | 56.81 | 29.39 | 22.92 | 16.83 | 22.9 | 17.65 | 4.65 | ND | MD | ND | ND |

Each human volunteer subject was given either Retrovir® 100 mg six times in 24 hours (600 mg/day) or Aztec™ 300 mg twice in 24 hours (600 mg/day). This dosage level continued for seven days when blood samples were evaluated and compared on sampling day seven. On the sample day, the AZT should have achieved a steady state of concentration. At time zero on the sampling day, the final dose was given. For those patients receiving Retrovir®, 100 mg of AZT was given; for those subjects receiving Aztec™, 300 mg of AZT was given. At day seven blood samples were drawn at 0, 1, 2, 3, 4, 5, 6, 7, 8, 10, 12, 16, and 24 hours for patients receiving Aztec™, while blood samples were drawn at 0, 0.5, 1.0, 1.5, 2.0, 2.5, 3.0, 3.5, 4, 5, 6.5, 8, and 24 hours in patients receiving Retrovir®. The reason for the different time sampling was to accurately reflect AZT levels based on Retrovir®'s immediate release and Aztec™'s controlled release of AZT. Blood samples were drawn and processed Although the foregoing invention has been described in some detail by way of illustration and example for purposes of clarity of understanding, it will be obvious to one skilled in the art that certain changes and modifications may be practiced within the scope of the invention, as limited only by the scope of the appended claims.

What is claimed is:

1. A controlled release oral dosage formulation comprising an active drug, said active drug comprising a therapeutically effective amount of one or more members selected form the group consisting of: AZT, phosphorylated AZT, a pharmaceutically acceptable salt of AZT, and a pharmaceutically acceptable salt of phosphorylated AZT, wherein said formulation contain said active drug and are coated with an acid resistant or hydrophobic polymer, said polymer constituting 1–15 weight percent of the formulation, said formulation further containing hydrogel polymers in an amount of 1–20 weight percent and a lipid in the amount of 1–10 weight percent.

2. A controlled release oral dosage formulation, comprising:
   (a) an active drug comprising granules of a therapeutically effective amount of one or more members selected form the group consisting of: AZT, phosphorylated AZT, a pharmaceutically acceptable salt of AZT, and a pharmaceutically acceptable salt of phosphorylated AZT;
   (b) one or more polymer coatings comprising one or more members selected from the group consisting of: an acid resistant polymer and a hydrophobic polymer, said one or more coatings being provided serially on said granules to form coated granules;
   (c) one or more hydrogel polymers; and
   (d) one or more lipids,
wherein said coated granules are blended with said hydrogel polymers and with said lipids.

3. The controlled release oral dosage formulation of claim 2, wherein said active drug is present in an amount of from 10 to 75 weight percent of the formulation, said acid resistant polymers and said hydrophobic polymers are present in an amount of from 1 to 15 weight percent of the formulation, said hydrogel polymers are present in an amount of from 1 to 20 weight percent of the formulation, and said lipids are present in an amount of from 1 to 10 weight percent of the formulation.

4. The controlled release oral dosage formulation of any one of claims 1 or 2, wherein said active drug further comprises a second therapeutic agent.

5. The controlled release oral dosage formulation of claim 4, wherein said second therapeutic agent comprises one or more members selected from the group consisting of: a nucleoside analog, acyclic nucleoside, interferon, renal excretion inhibitor, nucleoside transport inhibitor, immunomodulator, granulocyte macrophage colony stimulating factor, gancyclovir, phosphonate, a sodium salt of a phosphonate, and a magnesium salt of a phosphonate.

6. The controlled release oral dosage formulation of any one of claims 1 or 2, wherein said formulation is a tablet.

7. The controlled release oral dosage formulation of any one of claims 1 or 2, wherein said one or more polymeric coating further comprise a plastizer and an anti-adherant.

8. A method of treating HIV infection in an HIV seropositive patient, comprising a administering to said patient the controlled release oral dosage formulation of any one of claims 1, 2, or 3.

9. A method for preparing a controlled release rate solid oral dosage formulation comprising an active drug, said active drug comprising a therapeutically effective amount of one or more members selected form the group consisting of: AZT, phosphorylated AZT, a pharmaceutically acceptable salt of AZT, and a pharmaceutically acceptable salt of phosphorylated AZT, said method comprising:
   (a) blending said active drug with one or more pharmaceutically acceptable excipients to form a mixture;
   (b) dividing the resultant mixture of step (a) into one or more fractions;
   (c) separately granulating each of said one or more fractions of step (b) to form one or more granulated fractions;
   (d) coating the granules of each of said one or more granulated fractions of step (c) with one or more polymer coats applied serially, each of said polymer coats comprising one or more members selected from the group consisting of an acid resistant polymer and a hydrophobic polymer, to form coated granules; and
   (e) blending the resultant coated granules of step (d) with one or more hydrogel polymers and with one or more lipids, to form a final blended mixture.

10. A method for preparing a controlled release rate solid oral dosage formulation comprising an active drug, said active drug comprising a therapeutically effective amount of one or more members selected form the group consisting of: AZT, phosphorylated AZT, a pharmaceutically acceptable salt of AZT, and a pharmaceutically acceptable salt of phosphorylated AZT, said method comprising:
   (a) blending said active drug with one or more hydrogel polymers, one or more lipids and one or more pharmaceutically acceptable excipients to form a mixture;
   (b) granulating the resultant mixture of step (a) to form granules; and
   (c) coating the resultant granules of step(b) with one or more polymer coats applied serially, each of said polymer coats comprising one or more members selected from the group consisting of an acid-resistant polymer and a hydrophobic polymer to form a final blended mixture.

11. The method of claim 9, wherein said granulating step and coating of a first serial polymer coat are performed simultaneously.

12. The method of claim 10, wherein said step (b) comprises polymerization of said hydrogels with an alkaline monophosphate buffer and wherein step (c) comprises a secondary granulation and said polymer coat comprises one coat, said coat comprising the hydrophobic polymer ethyl cellulose.

13. The method of any one of claims 9–11 or 12, further comprising providing a second therapeutic agent in said mixture of step (a) or providing said second therapeutic agent in any one of said one or more polymer coats.

14. The method of any one of claims 9–11 or 12, further comprising the step of:
   compressing the final blended mixture into a tablet.

15. The controlled release oral dosage formulation of claim 5, wherein said nucleoside analog is a 2',3'-dideoxynucleoside.

16. A method of treating HIV infection in an HIV seropositive patient, comprising administering to said patient the controlled release oral dosage formulation of claim 4.

* * * * *